United States Patent
Turner et al.

(10) Patent No.: US 9,551,030 B2
(45) Date of Patent: Jan. 24, 2017

(54) FILTER ARCHITECTURE FOR ANALYTICAL DEVICES

(71) Applicant: Pacific Biosciences of California, Inc., Menlo Park, CA (US)

(72) Inventors: Stephen Turner, Menlo Park, CA (US); Mark McDonald, Milpitas, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 804 days.

(21) Appl. No.: 13/919,643

(22) Filed: Jun. 17, 2013

(65) Prior Publication Data

US 2013/0338010 A1 Dec. 19, 2013

Related U.S. Application Data

(60) Provisional application No. 61/756,935, filed on Jan. 25, 2013, provisional application No. 61/660,776, filed on Jun. 17, 2012.

(51) Int. Cl.

| | |
|---|---|
| *C12M 1/00* | (2006.01) |
| *C12M 1/34* | (2006.01) |
| *C12Q 1/68* | (2006.01) |
| *G01N 21/64* | (2006.01) |
| *G09G 5/00* | (2006.01) |
| *G02F 1/1335* | (2006.01) |
| *B01L 3/00* | (2006.01) |

(52) U.S. Cl.
CPC ........... *C12Q 1/6874* (2013.01); *G01N 21/648* (2013.01); *G01N 21/6428* (2013.01); *G01N 21/6454* (2013.01); *B01L 3/502715* (2013.01); *G01N 2021/6421* (2013.01); *G01N 2021/6441* (2013.01); *G01N 2021/6463* (2013.01); *G01N 2021/6471* (2013.01); *G01N 2021/6482* (2013.01); *G01N 2021/6484* (2013.01)

(58) Field of Classification Search
CPC ............ C12Q 1/68; G01N 21/64; C12M 1/34; G02B 6/26; G01J 5/02
USPC .................. 435/6.1, 283.1, 287.2; 422/82.08; 536/23.1, 24.3; 156/67; 250/208.1, 250/559.04, 559.05; 345/613, 694; 382/194; 349/95, 104, 108
See application file for complete search history.

(56) References Cited

U.S. PATENT DOCUMENTS

| | | |
|---|---|---|
| 6,255,083 B1 | 7/2001 | Williams |
| 6,917,726 B2 | 7/2005 | Levene et al. |
| 7,013,054 B2 | 3/2006 | Levene et al. |
| | (Continued) | |

OTHER PUBLICATIONS

U.S. Appl. No. 13/920,037, filed Jun. 17, 2013, Saxena et al.
(Continued)

*Primary Examiner* — Narayan Bhat
(74) *Attorney, Agent, or Firm* — David C. Scherer; Robert H. Reamey

(57) ABSTRACT

An approach to the design of the set of filters which allows for the collection of a larger portion of the optical signal while still distinguishing the presence of the various fluorophores is described. In some embodiments, the filter sets of the invention each block a smaller portion of the spectrum, allowing for a larger portion of the emitted light to be detected. The combined information from the light passing through two or more of the filters is then used to determine the presence of a given fluorophore. The filter sets of the invention can be particularly useful in integrated devices in which the light from a single molecule reaction in a small reaction region is directed to a detector or to a specific portion of a detector.

23 Claims, 7 Drawing Sheets

(56) References Cited

U.S. PATENT DOCUMENTS

| | | |
|---|---|---|
| 7,056,661 B2 | 6/2006 | Korlach et al. |
| 7,170,050 B2 | 1/2007 | Turner et al. |
| 7,224,540 B2 * | 5/2007 | Olmstead ............ G06K 7/10702 235/462.41 |
| 7,486,865 B2 | 2/2009 | Foquet et al. |
| 7,630,073 B2 | 12/2009 | Lundquist et al. |
| 7,692,783 B2 | 4/2010 | Lundquist et al. |
| 7,714,303 B2 | 5/2010 | Lundquist et al. |
| 7,715,001 B2 | 5/2010 | Lundquist et al. |
| 7,805,081 B2 | 9/2010 | Lundquist et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 7,907,800 B2 | 3/2011 | Foquet et al. |
| 7,961,314 B2 | 6/2011 | Lundquist et al. |
| 8,053,742 B2 | 11/2011 | Lundquist et al. |
| 8,149,399 B2 | 4/2012 | Lundquist et al. |
| 8,207,509 B2 | 6/2012 | Lundquist et al. |
| 8,318,094 B1 | 11/2012 | Bayandorian et al. |
| 8,703,422 B2 * | 4/2014 | Tomaney ............. C12Q 1/6869 435/6.12 |
| 9,252,175 B2 * | 2/2016 | Savoy ............... H01L 27/14625 |
| 2008/0030628 A1 * | 2/2008 | Lundquist ................ G01J 3/02 348/751 |
| 2008/0080059 A1 | 4/2008 | Dixon et al. |
| 2011/0256618 A1 | 10/2011 | Eid et al. |
| 2011/0270092 A1 * | 11/2011 | Kang ................... A61B 5/0071 600/476 |
| 2011/0278475 A1 | 11/2011 | Lundquist et al. |
| 2012/0014837 A1 | 1/2012 | Fehr et al. |
| 2012/0015825 A1 * | 1/2012 | Zhong ................ G01N 21/6428 506/6 |
| 2012/0019828 A1 | 1/2012 | McCaffrey et al. |
| 2012/0021525 A1 | 1/2012 | Fehr et al. |
| 2012/0085894 A1 | 4/2012 | Zhong et al. |

OTHER PUBLICATIONS

Eid et al., "Real-Time DNA Sequencing from Single Polymerase Molecules," Science (2009) 323:133-138.
Levene et al., "Zero-mode Waveguides for Single-molecule Analysis at High Concentration" Science (2003) 299:682-686.
International Search Report and Written Opinion dated Sep. 4, 2013 for related case PCT/US2013/046168.
International Preliminary Report on Patentability dated Dec. 31, 2014 for related case PCT/US2013/046168.

* cited by examiner

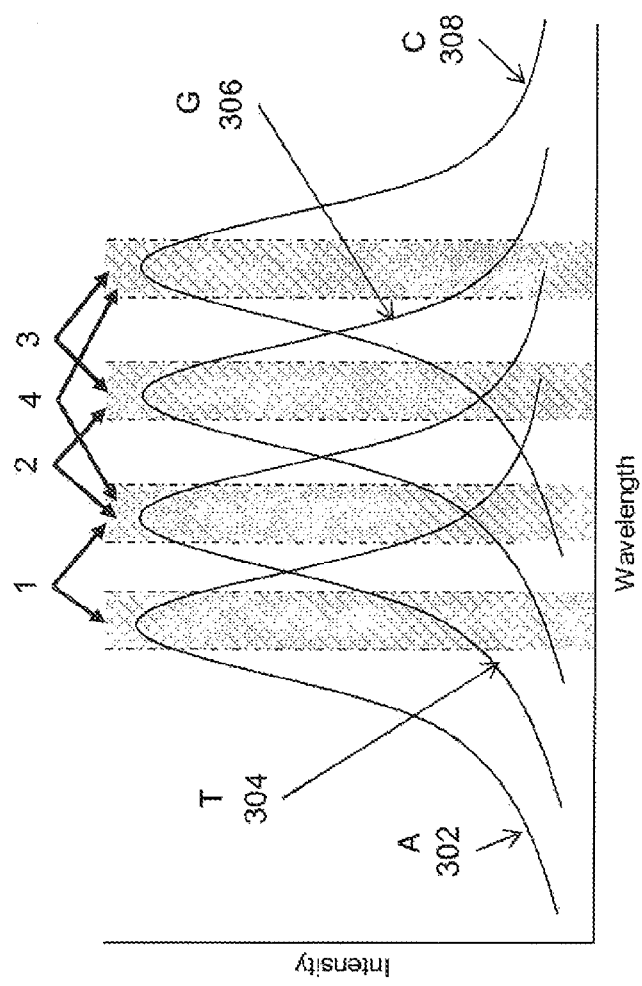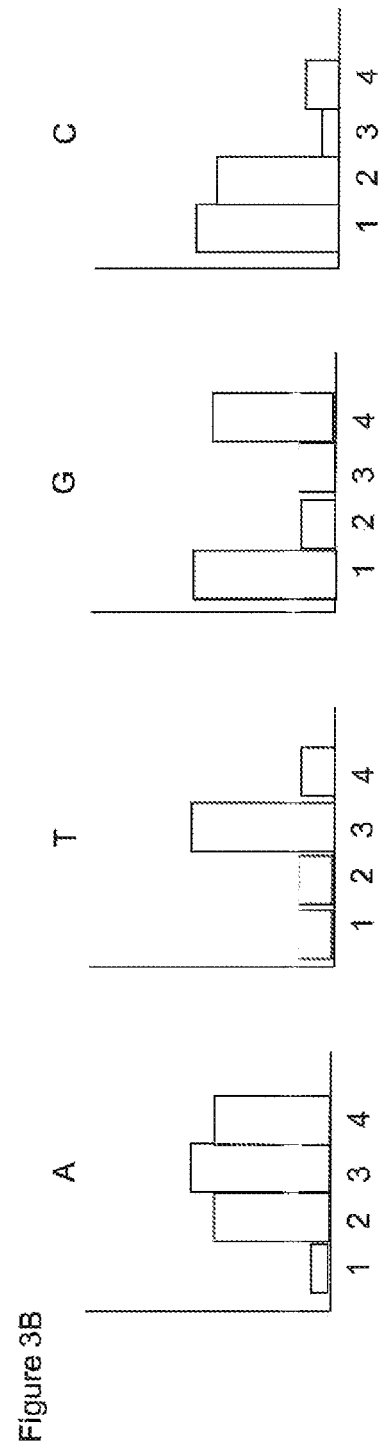
Figure 3A
Figure 3B

FILTER ARCHITECTURE FOR ANALYTICAL DEVICES

CROSS-REFERENCE TO RELATED APPLICATIONS

This application claims the benefit of U.S. Provisional Application No. 61/660,776, filed Jun. 17, 2012, and U.S. Provisional Application No. 61/756,935 filed Jan. 25, 2013, the disclosures of which are incorporated herein by reference in their entireties for all purposes.

STATEMENT REGARDING FEDERALLY SPONSORED RESEARCH

Not Applicable.

BACKGROUND OF THE INVENTION

Analytical technologies continue to advance far beyond the test tube scale evaluations of the 19th and 20th centuries, and have progressed to the point where researchers can look at very specific interactions in vivo, in vitro, at the cellular level, and even at the level of individual molecules. This progression is driven not just by the desire to understand important reactions in their purest form, but also by the realization that seemingly minor or insignificant reactions in living systems can prompt a cascade of other events that could potentially unleash a life or death result.

In this progression, these analyses not only have become more focused on lesser events, but also have had to become appropriately more sensitive, in order to be able to monitor such reactions. In increasing sensitivity to the levels of cellular or even single molecular levels, one may inherently increase the sensitivity of the system to other non-relevant signals, or 'noise'. In some cases, the noise level can be of sufficient magnitude that it partially or completely obscures the desired signals, i.e., those corresponding to the analysis of interest. Accordingly, it is desirable to be able to increase sensitivity of detection while maintaining the signal-to-noise ratio.

There is a continuing need to increase the performance of analytical systems and reduce the cost associated with manufacturing and using the system. In particular, there is a continuing need to increase the throughput of analytical systems. There is a continuing need to reduce the size and complexity of analytical system. There is a continuing need for analytical systems that have flexible configurations and are easily scalable.

The present invention provides devices, systems and methods for overcoming the above problems in addition to other benefits.

BRIEF SUMMARY OF THE INVENTION

In some aspects the invention provides an analytical device for detecting a plurality of different optical signals from reactions of interest each comprising a number of reaction events occurring over a time comprising; a substrate comprising an array of reaction regions each comprising a reaction mixture that each produce N distinct optical signals wherein N is 3 or greater, each of the N optical signals corresponding to one of N different reactive species, wherein an optical signal from one of the N reactive species indicates a reaction event occurring with that reactive species; and one or more detectors positioned in optical communication with the array of reaction regions for receiving the N distinct optical signals from each reaction region, the one or more detectors comprising N different pixel subsets for each reaction region, wherein each of the N pixel subsets has a different filter that permits a fraction of greater than 1/N of light from the optical signals impinging upon the filter to pass through to the pixel subset.

In some embodiments N is 4. In some embodiments each of the filters permits greater than 40% of light from the optical signals impinging upon the filters to pass through. In some embodiments each of the filters permits greater than 60% of light from the optical signals impinging upon the filters to pass through.

In some embodiments the device has one detector.

In some embodiments the device is for nucleic acid sequencing and the reaction regions each comprise a single polymerase enzyme complex comprising a polymerase enzyme and an template nucleic acid.

In some embodiments the array of reaction regions is integrated with the detector. In some embodiments the array of reaction regions is irreversibly integrated with the detector.

In some embodiments the N distinct optical signals comprise fluorescent signals and the analytical device further comprises an integrated waveguide for illumination of the array of reaction regions.

In some aspects the invention provides an analytical device, comprising: an array of reaction regions, each comprising a reaction mixture characterized by the presence of N different labels, each label providing an emission spectrum, each emission spectrum having a maximum; one or more detectors provided in optical communication with the array of reaction regions, the one or more detectors comprising a plurality of pixels with N pixel subsets, wherein N is 3 or greater: each pixel subset having a different filter wherein each filter has one or more blocking bands, each of which blocks a wavelength region including the emission maxima of from 1 to N-2 of the labels, wherein each filter blocks the emission maxima of a different label or of a different combinations of labels than each other filter.

In some embodiments each of the filters blocks the emission maximum of a different label. In some embodiments each of the filters blocks the emission maximum of at least two labels. In some embodiments N is 4.

In some embodiments the device has one detector.

In some embodiments the device is used for nucleic acid sequencing and the reaction regions each comprise a single polymerase enzyme complex comprising a polymerase enzyme and an template nucleic acid.

In some embodiments the array of reaction regions is integrated with the detector. In some embodiments the array of reaction regions is irreversibly integrated with the detector. In some embodiments the emission spectra comprise fluorescent signals and the analytical device further comprises an integrated waveguide for illumination of the array of reaction regions.

In some aspects the invention provides an analytical device, comprising: an array of reaction regions, each comprising a reaction mixture characterized by the presence of 4 different labels, each label providing an emission spectrum, each emission spectrum having a maximum; one or more detectors provided in optical communication with the array of reaction regions, the one or more detectors comprising a plurality of pixels with 4 pixel subsets for each reaction region: each of the 4 pixel subsets comprising a different filter wherein each filter has one or more blocking bands that each block a wavelength region including the emission maxima of the optically detectable spectrum of one or two, but not three of the 4 labels, wherein each blocking filter blocks the emission maxima of a different label or of a different combination of labels.

In some embodiments the device has one detector.

In some embodiments the reaction regions each comprise a single polymerase enzyme complex comprising a polymerase enzyme and a template nucleic acid and the labels are fluorescent labels on nucleotide analogs.

In some embodiments each of the filters blocks the emission maximum of a different label. In some embodiments each of the filters blocks the emission maximum of at least two labels. In some embodiments the array of reaction regions is integrated with the detector. In some embodiments the array of reaction regions is irreversibly integrated with the detector.

In some embodiments the emission spectra comprise fluorescent signals and the analytical device further comprises an integrated waveguide for illumination of the array of reaction regions.

In some aspects the invention provides an analytical system comprising an analytical device described herein, an illumination system for providing excitation light to the array of reaction regions comprising an illumination source and illumination optical components, detection optical components for directing light to the one or more detectors, and a computer system in contact with the detectors for obtaining sequencing information from detected signals.

In some aspects the invention provides an analytical device for detecting a plurality of different optical signals from a reaction of interest comprising: an array of reaction regions each comprising a reaction mixture that produces 4 distinct optical signals, each of the 4 optical signals corresponding to one of 4 different reactive species, wherein an optical signal from one of the reactive species indicates a reaction event occurring with that reactive species; and one or more detectors positioned in optical communication with the array of reaction regions comprising pixel subsets 1, 2, 3, and 4; wherein pixel subset 1 comprises filter 1 having wavelength blocking band 1 that blocks light from $\lambda 1i$ to $\lambda 1f$, pixel subset 2 comprises filter 2 that has wavelength blocking band 2 that blocks light from $\lambda 2i$ to $\lambda 2f$, pixel subset 3 comprises filter 3 that has wavelength blocking band 3 that blocks light from $\lambda 3i$ to $\lambda 3f$, pixel subset 4 comprises filter 4 that has wavelength blocking band 4 that blocks light from $\lambda 4i$ to $\lambda 4f$, wherein $\lambda 1i > \lambda 1f$, $\lambda 2i > \lambda 2f$, $\lambda 3i > \lambda 3f$, and $\lambda 4i > \lambda 4f$; and wherein each of the wavelength blocking bands blocks 80% or greater of the light between wavelengths $\lambda i$ and $\lambda f$ for that band, and wherein each of the filters transmits 50% or greater of the light between $\lambda 1i$ and $\lambda 4f$ outside of its blocking band.

In some embodiments $\lambda 1i > \lambda 1f \geq \lambda 2i > \lambda 2f \geq \lambda 3i > \lambda 3f \geq \lambda 4i > \lambda 4f$.

In some embodiments the device has one detector. In some embodiments the device is used for nucleic acid sequencing wherein the reaction regions each comprise a single polymerase enzyme complex comprising a polymerase enzyme and a template nucleic acid and the labels are fluorescent labels on nucleotide analogs. In some embodiments the array of reaction regions is integrated with the detector. In some embodiments the array of reaction regions is irreversibly integrated with the detector. In some embodiments the emission spectra comprise fluorescent signals and the analytical device further comprises an integrated waveguide for illumination of the array of reaction regions.

In some embodiments each of the filters transmits 60% or greater of the light between $\lambda 1i$ and $\lambda 4f$ outside of its blocking band. In some embodiments each of the filters transmits 70% or greater of the light between $\lambda 1i$ and $\lambda 4f$ outside of its blocking band. In some embodiments each of the filters transmits 80% or greater of the light between $\lambda 1i$ and $\lambda 4f$ outside of its blocking band.

In some aspects the invention provides an analytical device for detecting a plurality of different optical signals from a reaction of interest comprising: an array of reaction regions each comprising a reaction mixture that produces 4 distinct optical signals, each of the 4 optical signals corresponding to one of 4 different reactive species, wherein an optical signal from one of the reactive species indicates a reaction event occurring with that reactive species, wherein the range of wavelengths produced includes wavelengths between $\lambda 1i$ and $\lambda 4f$; and one or more detectors positioned in optical communication with the array of reaction regions comprising pixel subsets 1, 2, 3, and 4; wherein pixel subset 1 comprises filter 1, pixel subset 2 comprises filter 2, pixel subset 3 comprises filter 3, pixel subset 4 comprises filter 4, wherein each of filters 1, 2, 3, and 4 comprises a pair of different wavelength blocking bands 1, 2, 3, or 4 wherein wavelength blocking band 1 blocks light from $\lambda 1i$ to $\lambda 1f$, wavelength blocking band 2 blocks light from $\lambda 2i$ to $\lambda 2f$, wavelength blocking band 3 blocks light from $\lambda 3i$ to $\lambda 3f$, wavelength blocking band 4 blocks light from $\lambda 4i$ to $\lambda 4f$, wherein $\lambda 1i > \lambda 1f \geq \lambda 2i > \lambda 2f \geq \lambda 3i > \lambda 3f \geq \lambda 4i > \lambda 4f$; and wherein each of the wavelength blocking bands blocks 80% or greater of the light between wavelengths $\lambda i$ and $\lambda f$ for that band, and wherein each of the filters transmits 50% or greater of the light between $\lambda 1i$ and $\lambda 4f$ outside of the wavelength blocking bands for that filter, and wherein the pair of wavelength blocking bands in each of the four filters is different from the pair of wavelength blocking bands in each of the other filters.

In some embodiments $\lambda 1i > \lambda 1f \geq \lambda 2i > \lambda 2f \geq \lambda 3i > \lambda 3f \geq \lambda 4i > \lambda 4f$.

In some embodiments the device has one detector. In some embodiments the device is for nucleic acid sequencing wherein the reaction regions each comprise a single polymerase enzyme complex comprising a polymerase enzyme and a template nucleic acid and the labels are fluorescent labels on nucleotide analogs.

In some embodiments the array of reaction regions is integrated with the detector. In some embodiments the array of reaction regions is irreversibly integrated with the detector. In some embodiments the emission spectra comprise fluorescent signals and the analytical device further comprises an integrated waveguide for illumination of the array of reaction regions.

In some embodiments each of the filters transmits 60% or greater of the light between $\lambda 1i$ and $\lambda 4f$ outside of its blocking band. In some embodiments each of the filters transmits 70% or greater of the light between $\lambda 1i$ and $\lambda 4f$ outside of its blocking band. In some embodiments each of the filters transmits 80% or greater of the light between $\lambda 1i$ and $\lambda 4f$ outside of its blocking band.

In some aspects the invention provides an integrated analytical device for nucleic acid sequencing, comprising: an array of reaction regions, each comprising a single immobilized polymerase enzyme complex comprising a polymerase enzyme and a primed template nucleic acid; each reaction region comprising a reaction mixture characterized by the presence of 4 different fluorescent labels, each label corresponding to one of four nucleotide analogs, each label providing an emission spectrum, each emission spectrum having a maximum;

one or more waveguides for illumination of the array of reaction regions;

a detector comprising a plurality of pixels with 4 pixel subsets for each reaction region: the detector in optical communication with the array of reaction regions; each of the 4 pixel subsets comprising a different filter wherein each filter has one or more blocking bands that each block a wavelength region including the emission maxima of one or two, but not three of the 4 labels, wherein each blocking filter blocks the emission maxima of a different label or of a different combination of labels.

In some embodiments each of the filters blocks the emission maximum of a different label. In some embodiments each of the filters blocks the emission maximum of at least two labels. In some embodiments each of the filters permits greater than 25% of light from the optical signals impinging upon the filters to pass through. In some embodiments each of the filters permits greater than 40% of light from the optical signals impinging upon the filters to pass through. In some embodiments each of the filters permits greater than 60% of light from the optical signals impinging upon the filters to pass through. In some embodiments the components are irreversibly integrated.

In some aspects the invention provides an analytical instrument comprising: an integrated device as described herein; an illumination source for providing illumination light to the one or more waveguides, an electronic system for providing voltage and current to the detector, and for receiving signals from the detector; and a computer system for analyzing the signals from the detector to obtain sequence information about the template nucleic acid.

In some aspects the invention provides a method for detecting a plurality of different optical signals from reactions of interest each comprising a number of reaction events occurring over a time comprising; providing a substrate comprising an array of reaction regions each comprising a reaction mixture that each produce N distinct optical signals wherein N is 3 or greater, each of the N optical signals corresponding to one of N different reactive species, wherein an optical signal from one of the N reactive species indicates a reaction event occurring with that reactive species; and detecting the N optical signals at one or more detectors positioned in optical communication with the array of reaction regions for receiving the N distinct optical signals from each reaction region, the one or more detectors comprising N different pixel subsets for each reaction region, wherein each of the N pixel subsets has a different filter that permits a fraction of greater than 1/N of light from the optical signals impinging upon the filter to pass through the pixel subset.

In some embodiments N is 4. In some embodiments each of the filters permits greater than 40% of light from the optical signals impinging upon the filters to pass through. In some embodiments each of the filters permits greater than 60% of light from the optical signals impinging upon the filters to pass through. In some embodiments the method uses one detector.

In some embodiments the reaction regions each comprise a single polymerase enzyme complex comprising a polymerase enzyme and an template nucleic acid.

In some embodiments the array of reaction regions is integrated with the detector.

In some embodiments the array of reaction regions is irreversibly integrated with the detector. In some embodiments the N distinct optical signals comprise fluorescent signals and the system further comprises an integrated waveguide for illumination of the array of reaction regions.

In some aspects the invention provides a method for monitoring an analytical reaction, comprising: providing an analytical device having an array of reaction regions, each comprising a reaction mixture characterized by the presence of N different labels, each label providing an emission spectrum, each emission spectrum having a maximum; detecting the emission spectra with one or more detectors in optical communication with the array of reaction regions, the one or more detectors comprising a plurality of pixels with N pixel subsets, wherein N is 3 or greater: each pixel subset having a different filter wherein each filter has one or more blocking bands, each of which blocks a wavelength region including the emission maxima of from 1 to N−2 of the labels, wherein each filter blocks the emission maxima of a different label or of a different combination of labels than each other filter; and monitoring the signals detected at each pixel subset to monitor the analytical reaction.

In some embodiments each of the filters blocks the emission maximum of a different label. In some embodiments each of the filters blocks the emission maximum of at least two labels. In some embodiments N is 4. In some embodiments the method uses one detector.

In some embodiments the method is a method of nucleic acid sequencing wherein the reaction regions each comprise a single polymerase enzyme complex comprising a polymerase enzyme and an template nucleic acid.

In some embodiments the array of reaction regions is integrated with the detector.

In some embodiments the array of reaction regions is irreversibly integrated with the detector. In some embodiments the emission spectra comprise fluorescent signals and the method further comprises an integrated waveguide for illumination of the array of reaction regions.

In some aspects the invention provides a method for nucleic acid sequencing, comprising: providing an analytical device having an array of reaction regions, each comprising a single immobilized polymerase enzyme complex comprising a polymerase enzyme and a primed template nucleic acid; each reaction region comprising a reaction mixture characterized by the presence of 4 different fluorescent labels, each label corresponding to one of four nucleotide analogs, each label providing an emission spectrum, each emission spectrum having a maximum; illuminating the array of reaction regions with one or more waveguides; and detecting emission spectra with a detector comprising a plurality of pixels with 4 pixel subsets for each reaction region; each of the 4 pixel subsets comprising a different filter wherein each filter has one or more blocking bands that each block a wavelength region including the emission maxima of one or two, but not three of the 4 labels, wherein each blocking filter blocks the emission maxima of a different label or of a different combination of labels.

In some embodiments each of the filters blocks the emission maximum of a different label. In some embodiments each of the filters blocks the emission maximum of at least two labels. In some embodiments each of the filters permits greater than 25% of light from the optical signals impinging upon the filters to pass through. In some embodiments each of the filters permits greater than 40% of light from the optical signals impinging upon the filters to pass through. In some embodiments each of the filters permits greater than 60% of light from the optical signals impinging upon the filters to pass through.

In some embodiments the components are irreversibly integrated.

BRIEF DESCRIPTION OF THE FIGURES

FIG. 3A schematically illustrates emission spectra of four distinct signal events, e.g., fluorescently labeled nucleotide analogs and illustrates the positions four blocking bands of the invention where each of four blocking filters 1-4 has two blocking bands; FIG. 3B schematically illustrates a signal profile at each of four detector elements each having one of filters 1-4.

DETAILED DESCRIPTION OF THE INVENTION

General

Figure 1A:
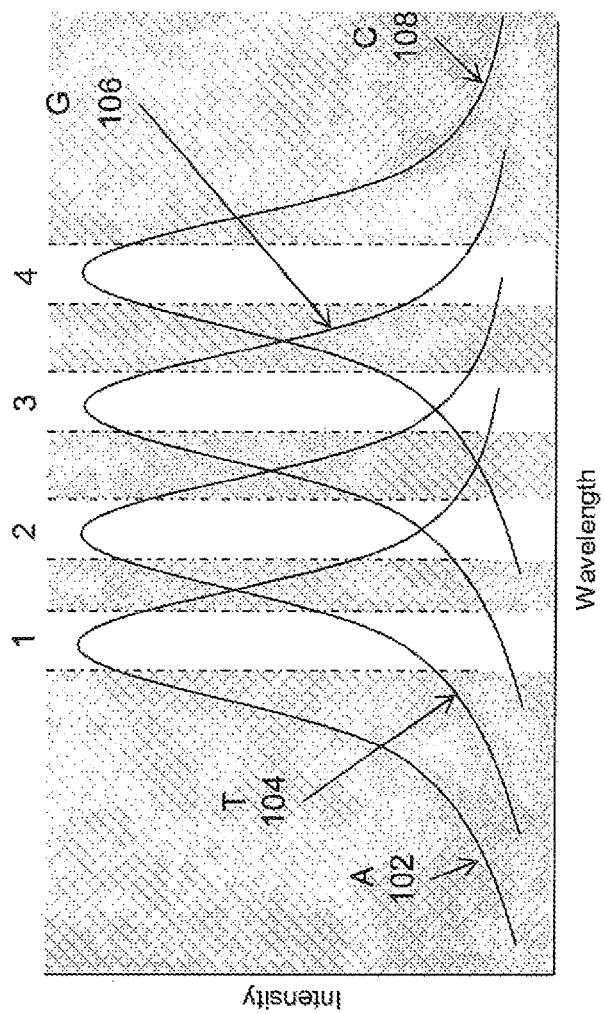
FIG. 1A schematically illustrates emission spectra of four distinct signal events, e.g., fluorescently labeled nucleotide analogs and illustrates the positions of conventional filters 1-4.

The present invention is generally directed to improved systems, devices and methods for performing analytical operations, and particularly optical analysis of chemical, biochemical and biological reactions for use in chemical, biological, medical and other research and diagnostic applications. The systems, devices and methods of the invention are particularly suited for application in integrated analytical components, e.g., where multiple functional components of the overall analysis system are co-integrated within a single modular component. However, as will be clear upon reading the following disclosure, a number of aspects of the invention will have broad utility outside of such integrated devices and systems.

In general, the optical analyses that are subject of the present invention, seek to gather and detect one or more optical signals from a reaction of interest, the appearance or disappearance of which, or localization of which, is indicative of a given chemical or biological reaction and/or the presence or absence of a given substance within a sample material. In some cases, the reactants, their products, or substance of interest (all of which are referred to as reactants herein) inherently present an optically detectable signal which can be detected. In other cases, reactants are provided with exogenous labeling groups to facilitate their detection.

One of the objects of the present invention is carrying out optical analyses involving discrimination of multiple optical signals using a larger portion of the emitted light than in conventional methods. The methods are particularly useful for the detection of multiple types of fluorophores in real time.

For example, consider an analytical device for monitoring a reaction having four types of fluorophores, each with distinct (but possibly overlapping) spectral signals. In a typical conventional approach, four color filters would be used. Each of the four filters would be designed block the spectral region corresponding to the three other fluorophores while letting in the light corresponding to the spectral region of the fluorophore of interest. While this process allows for measuring the presence of the fluorophore of interest, blocking the portion of the spectrum corresponding to the other three fluorophores can result in the loss of a large portion of the signal. This can be particularly problematic for monitoring analytical reaction such as single molecule reactions, where the amount of signal available can be extremely low, in some cases on the order of tens to hundreds of photons.

The current invention provides a different approach to the design of the set of filters which allows for the collection of a larger portion of the optical signal while still distinguishing the presence of the various fluorophores. The filter sets of the invention each block a smaller portion of the spectrum, allowing for a larger portion of the emitted light to be detected. The combined information from the light passing through two or more of the filters is then used to determine the presence of a given fluorophore.

The filter sets of the invention can be particularly useful in integrated devices in which the light from a single molecule reaction in a small reaction region is directed to a detector or to a specific portion of a detector.

The general overall architecture of the optical analysis systems of the invention typically includes a reaction region in which a reaction of interest is taking place. Light is delivered to the reaction region to excite fluorophores therein, and emitted light from the fluorophores is directed to a detector element. The optical signals impinging upon the detector element are then detected and recorded and subjected to analysis to determine their relevance to the underlying reaction of interest. Typically there will be many reaction regions, each region illuminated and emitting signals to a detector element.

As will be appreciated, the systems, devices and methods of the invention may be applied to analytical reaction regions having any of a wide variety of formats. For example, reaction regions may include defined and discrete fluid reservoirs, e.g., wells in a multi-well plate, channels in a micro fluidic device, discrete particles bearing localized reactants, or discrete locations on a planar or other substrate. The reaction regions will generally include some measure of confinement to retain a given reaction of interest in a set observable location. Such confinement may include structural confinements, e.g., structural barriers or walls that prevent movement of reactants, as in wells, chambers, channels, or the like, chemical confinements, e.g., linkers, binding groups or other chemical treatments that immobilize one or more reactants within a given location, particle based confinements, e.g., where based upon either or both of chemical and structural confinement, the reaction of interest is localized to one or more individual particles or beads, or other confining techniques, e.g., hydrophobic or hydrophilic regions that restrict the movement of aqueous materials. By confining the reaction of interest, one can assign iterative optical signals to the same reaction of interest, and thus monitor that reaction over time.

As a reaction of interest is carried out, it is typically configured to produce optical signals that are indicative of the progress of that reaction, i.e., is the reaction taking place, as well as provide information as to the nature of the reaction taking place, i.e., what reactants are participating in that reaction. As will be appreciated, a wide variety of analytical operations may be performed using the overall reaction framework described herein, and as a result, are applicable to the present invention. Such reactions include reactive assays, e.g., examining the combination of reactants to monitor the rate of production of a product or consumption of a reagent, such as enzyme reactions, catalyst reactions, etc. Likewise, associative or binding reactions may be monitored, where one is looking for specific association between two or more reactants, such as nucleic acid hybridization assays, antibody/antigen assays, coupling or cleavage assays, and the like. For ease of discussion, the invention is generally described in terms of a nucleic acid sequencing analysis.

Filter Architecture for Higher Levels of Photon Capture

In certain aspects, the invention provides devices, systems, and methods that employ a filter architecture that results in higher levels of photon capture than obtained with prior art approaches. The filter architectures of the instant invention are generally for observing analytical reactions having multiple spectrally distinct optical outputs, and in particular multiple spectrally distinct optical emissions over time. In such analytical reactions it can be desirable to identify whether one of multiple reactions is occurring over a given time period. The filter architectures of the present invention are particularly useful for analytical reactions having a very small amount of signal, for example for observing reactions at single molecule resolution. Two exemplary types of reaction for which the filter architecture of the instant invention is useful are nucleic acid sequencing including single molecule real time sequencing and binding assays including single molecule real-time binding assays.

In a conventional system for observing multiple spectrally distinct optical signals over time, typically a set of filters is employed in which each of the filters selectively allows the signal from one of the spectral signals while blocking the signal from the rest of the spectrum.

In addition to the above described approaches, the present invention optionally or additionally achieves more efficient signal detection, as well as optics simplification, through novel filter architectures and signal processing approaches. In particular, as noted above, typical four color detection schemes operate through the detection of signal at a narrow spectral band corresponding to and correlating with an emission signal maximum emitted from a particular reaction event, e.g., incorporation of a single type of nucleotide in a sequencing operation, with the remainder of the spectrum being blocked and disregarded. In the context of single molecule analyses and/or small scale integrated devices, however, where signal detection efficiency is of far greater importance, discarding of any photons associated with a particular reaction event should be avoided as much as possible.

One approach to this aspect of the present invention is illustrated in the context of multicolor fluorescence detection systems, e.g., the four color fluorescence systems described above. As noted, typically, such systems include reactions that produce different optical signals based upon the occurrence of different reaction events, such as incorporation of different fluorescently labeled nucleotides in many nucleic acid 'sequencing by synthesis' applications.

Signals that are indicative of the addition of a given base to the polymerase/template/primer replication complex are typically passed through a series of optical filters that narrowly separate out each signal component based upon the signal in a region near its spectral maximum. That signal component is directed to a separate detector or sensing region of a detector, e.g., a pixel or subset of pixels in an array detector. The type of base added in a given step is then identified from the narrow signal component that is detected at that particular juncture in the assay. While this method is highly effective for many applications, where signal is very limited, e.g., where attempting to detect signal from a very small reaction volume or a single molecule of a fluorescent label, narrowly attenuating that signal becomes more problematic.

The potential difficulties with the conventional approach are schematically illustrated in FIG. 1 with reference to an exemplary four color nucleic acid sequencing system. As shown in FIG. 1A, the signal palette for the four bases in an exemplary DNA sequencing reaction are shown as four distinct, albeit partially overlapping emission maxima 102, 104, 106 and 108. Each of the signals corresponds to a different fluorescent species which is attached to one of the nucleotides e.g. A, T, G, and C. In this example, 102 is the emission of a label attached to nucleotide A, 104 is T, 106 is G, and 108 is C. In conventional four color detection systems, signals from the reaction zone are passed through a filter system, typically comprised of multiple filters, each of which allow a narrow spectral band, e.g., spectral band 1, 2, 3 or 4, that corresponds to region around an emission maximum for each differently labeled nucleotide (e.g., A (102), T (104), G (106), and C (108), respectively) to reach one of four different detector elements or detection zones (or pixel subsets) on the detector. For convenience, different detectors or different detection zones on the same detector are interchangeably referred to herein as different "detectors". For example, a device having multiple reaction regions may have a detector with detection zones corresponding to each reaction region. In some cases, the detection zone corresponding to a reaction region may be referred to as the detector.

Figure 1B:
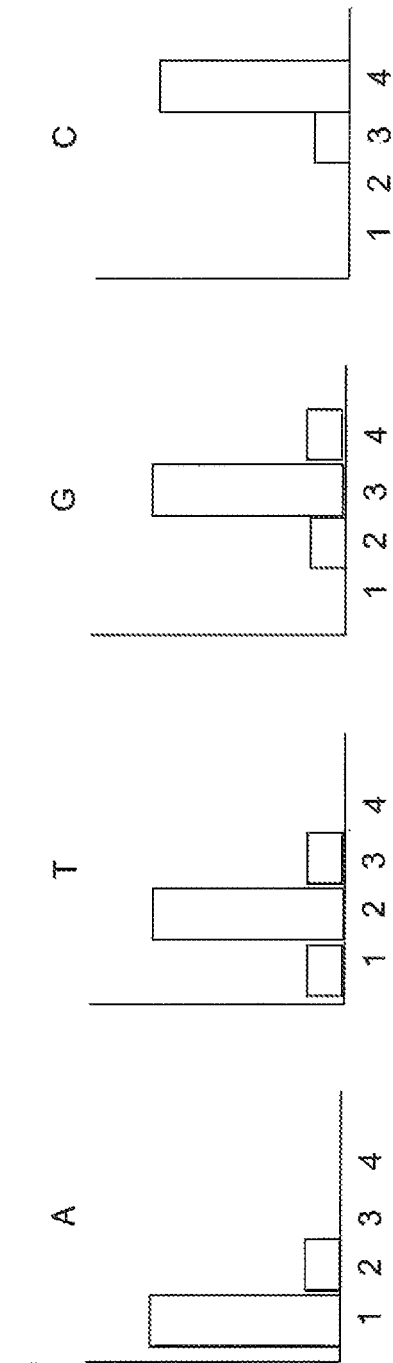
FIG. 1B schematically illustrates a signal profile at each detector element based upon a typical four color separation scheme.

FIG. 1B shows a schematic illustration of a signal profile for each base, based upon such conventional systems. As shown, e.g., for an A base incorporation, a signal for a given base is detected largely by detector 1, while being blocked from or significantly attenuated at detectors 2, 3 and 4. The same is true for each of the four bases as shown in FIG. 1B.

This technique can be effective, for example where signals of a given spectral band are sufficiently separated from other signals and the separated signals are directed to a detector where all light associated with that signal can be detected. However, for each set of sub-pixels that is responsible for identifying the presence of a particular labeled nucleotide, only the photons most likely to correspond to that label are allowed to pass through the filter, and the remaining photons are rejected. While this approach can provide the ability to correctly call the identity of a given labeled base, it does so by throwing away a large portion of the available light signal. The loss of this light can be costly. For example, in observing single molecule systems, sometimes tens to hundreds of photons are relied on to identify an incorporation event. Being able to collect more photons can allow for more correctly identifying bases for sequencing. This is particularly the case for the integrated systems described herein where the detector is coupled directly to the reaction region from which the light is emitted. For these miniaturized systems, the ability to completely separate different signals and detect all light associated with the separated components is impaired by the structural size of the devices. In particular, signal 'separation' in certain implementations of integrated devices may fractionate a signal and subject each fraction to a different filter set, in order to distinguish different signals.

For example, the conventional approach can work well where light from each of the given wavelength bands is directed to a different detector or each is directed to a different region on a detector using conventional optics. In these cases, the light falling within each of the four bands is largely collected. In an integrated system such as described herein, where specifically directing the various wavelength bands is not used, the losses in light due to only allowing a narrow slice of the spectrum through each color filter can be problematic.

The instant invention provides systems, device, and methods for identifying the labeled base that is present while collecting significantly more of the light from the labels. In accordance with the present invention, the filtering approach is "inverted" from the conventional approach. For example, instead of having four filters, each of which allow only the light associated with one label, in the instant invention, each of the four filters is a blocking filter for the wavelength range corresponding to the maximum emission of each label, substantially blocking the light from one label, while allowing the light from the other three labels (if present) through. The determination of which label is present is then indicated which combination of sub-pixel sets detects the presence of light.

Figure 2A:
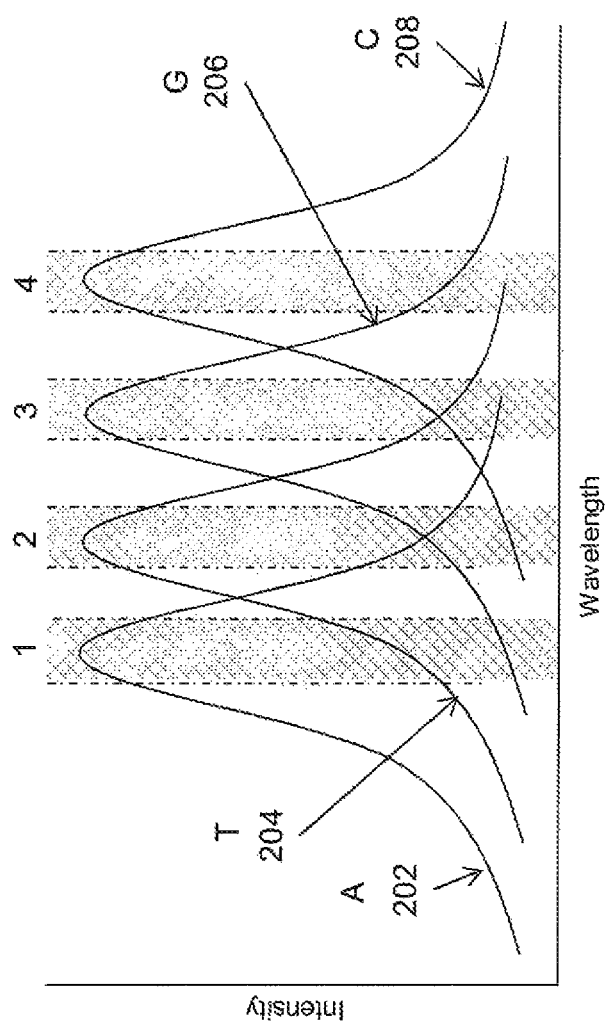
FIG. 2A schematically illustrates emission spectra of four distinct signal events, e.g., fluorescently labeled nucleotide analogs and illustrates the positions four blocking filters of the invention.

Consider the system shown in FIG. 2. Here, as shown in FIG. 2A, blocking filters are provided at wavelength regions 1, 2, 3, and 4. The width of each of the blocking filters is shown as narrowly blocking the peak. The width of each of the filters can be tailored to obtain the desired quality signal. The wider the peaks, the more signal that is blocked resulting in fewer photons, but potentially providing greater discrimination.

For example, each filter for each of the different detectors or sensing elements represents a band blocking filter that only blocks the indicated portion of the spectrum, e.g., spectral band 1, 2, 3 and 4, from reaching its respective detector component. The blocking filters are positioned to block the region of the spectrum around the maxima of each of the emission spectra of the fluorescent species attached to each of the bases (e.g., filter 1 blocking A (202), filter 2 blocking T (204), filter 3 blocking G (206), and filter 4 blocking C (208), respectively). Accordingly, the presence of each signal results in detection at three of the four detection zones.

Figure 2B:
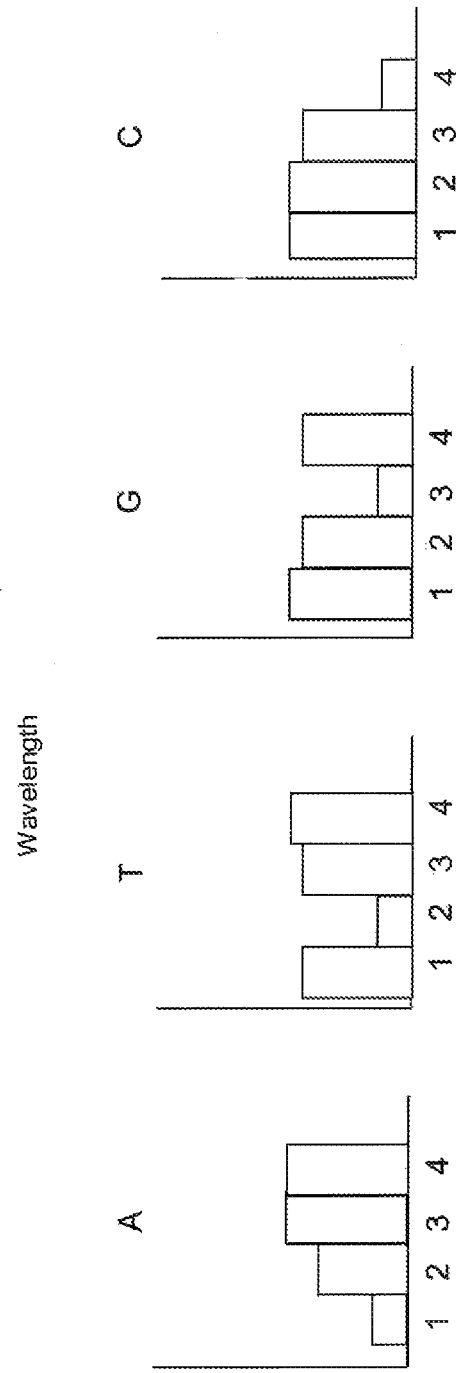
FIG. 2B schematically illustrates a signal profile at each of four detector elements each having one of filters 1-4.

FIG. 2B schematically shows the signal profile at each of the detectors for all four bases. Note, for example, the set of signals when the base A is present in the detection volume. In this case, filter 1 blocks band 1 corresponding to the main emission of the fluorescent label associated with A, and therefore the signal at label 1 is low. Detectors 3 and 4 have blocking bands that are substantially outside of the emission profile of fluorescent label associated with A, so each detector 3 and 4 measure substantially all of the photons from the fluorescent label. Detector 2 detects the light that passes through filter 2 which has blocking band 2. Blocking band 2 cuts off the edge of the emission spectrum, so detects most of the light emitted by the fluorescent label associated with A. The signal from the fluorescent label associated with each of the other three bases is also shown in FIG. 2B. Each signal event results in a greater amount of detected optical signal than would be provided in a signal profile from a conventional narrow-band pass filter architecture, e.g., as illustrated in FIG. 1B, above. The resulting unique signal profile over multiple detectors is then used to identify the nature of the fluorescent label, and consequently, the identity of the added base. In effect, such a filter scheme results in a 'negative' of the signal profile from the conventional narrow band-pass scheme. Although described in terms of four-color schemes, it will be appreciated that this approach can also be applied to fewer or greater than four color schemes, e.g., three-color schemes, five-color schemes, etc.

FIG. 3 shows an alternative embodiment of the invention in which more than one blocking band is used per filter. As with the other examples described above, this example shows four separate spectrally distinct emission signals (302-308), each corresponding to one of the four nucleobases, for example for use in single molecule real time sequencing. FIG. 3A shows that for each reaction region, there are four detector elements 1-4, each having a different filter 1-4 disposed above it such that any light reaching the detector element passes through the filter. Here, filter 1 has two blocking bands, one blocking emission 302 corresponding to A and emission 304 corresponding to T; filter 2 has two blocking bands, one blocking emission 304 corresponding to T and emission 306 corresponding to G; filter 3 has two blocking bands, one blocking emission 306 corresponding to G and emission 308 corresponding to C; filter 4 has two blocking bands, one blocking emission 304 corresponding to T and emission 308 corresponding to C.

FIG. 3B illustrates the output at each of the detector elements or channels 1-4 while one of the four labeled nucleotides is in the detection volume of the reaction region and emitting a signal. For example, when A is present, the signal from the fluorophore corresponding to A is substantially blocked by filter 1, but majority of the signal is not blocked by filters 2, 3, and 4. It can be seen in FIG. 3B that a characteristic set of signals is seen by using the signals at each of the four detectors. As with the filters having one blocking band described above, the width and position of each of the blocking bands can be modified in order to optimize the performance of the system. The specific selection of the two blocking bands for each of the filters in this example is not meant to be limiting. Any suitable combination of pairs of blocking bands can be used at each filter.

In addition, each filter need not have the same number of blocking bands. Any suitable combination can be used, for example, 1, 1, 1, 2; 1, 1, 2, 2; 1, 2, 2, 2, etc. In addition, the number of blocking bands independently at each of the filters can be 1, 2, 3, or more blocking bands.

It will be appreciated by those in the art that the emission spectra of fluorescent species can be broader and have more features than in the provided example. These features can be used as an advantage in the present detection methods. For any four spectrally distinct species, there will be a characteristic set of levels of intensity at each of the four channels. The known relative intensity levels can be used to for determining the presence of one of the known species in the detection volume of the device. By providing bands that specifically block certain regions of an emission spectrum, the combination of the intensities in each of the pixel subsets provides a characteristic signal that identifies the presence of a label.

For example, in some cases there are two blocking bands for a fluorescent label having two main emission maxima, one blocking band for one emission maximum, and a second blocking band for the second emission maximum. Similarly, a fluorescent label having 3 main emission maxima may have three blocking filters, each corresponding to one of the emission maxima. This approach of using multiple blocking bands for a single emitter can be used for 1, 2, 3, 4, 5, or more emission maxima. Where the system has multiple fluorescent labels, there can be multiple blocking bands for some labels, and single blocking bands for other labels.

The devices, methods, and systems of the invention are directed toward distinguishing different emitting species while collecting a high level of signal. For example, in some embodiments, there are four different detector elements or channels, and each detector element, e.g., pixel subset on a given detector, has a filter layer that permits greater than 25% of light from the totality of the various different optical signals impinging upon the filter layer to pass through to the detector or pixel subset. In some embodiments, the filter layer will permit greater than 40% of light from the totality of the various different optical signals impinging upon the filter layer to pass through the detector element, and in additional embodiments, greater than 50% of the light that impinges on the filter from the totality of optical signals will pass through a given filter layer to reach its associated detector element, and in some cases, greater than 60% of the light that impinges on the filter from the totality of optical signals will pass through a given filter layer to reach its associated detector element, and in additional embodiments, greater than 70% of the light that impinges on the filter from the totality of optical signals will pass through a given filter layer to reach its associated detector element.

The labels used in the system are typically fluorescent labels. Such labels can comprise, for example, quantum dots, fluorescent beads, dyes, fluorescent elements such as fluorescent lanthanides and transition metals.

In addition to benefits of increased signal at each detector, this aspect of the invention provides additional benefits in the context of integrated optical devices, e.g., devices in which at least the optical components, e.g., filters and the like, and detector elements are integrated into a single substrate. In particular, by providing a single narrow band blocking filter type, rather than a filter stack between the assay location and a given detector, one can greatly simplify the overall architecture of the device. In particular, by using only a single narrow band blocking filter, one can use single layers or single composition filter layers rather than hybrid filter layers or filter compositions Further, because fewer layers are provided between the assay region and the detector, one can provide the assay location in closer proximity to the detector, reducing the potential for signal loss, cross-talk, and other signal transmission difficulties that may be inherent in more complex optical trains. In particular, where a more conventional four color system might require a four layer optical filter at each detector, and result in a substantially attenuated signal, the systems described herein would include a single filter layer at each detector, and result in the higher level signal profiles described above.

The devices and systems of the invention may generally be characterized by virtue of the number of filter layers as it relates to the number of spectrally distinct optical signals to be detected.

Figure 4:
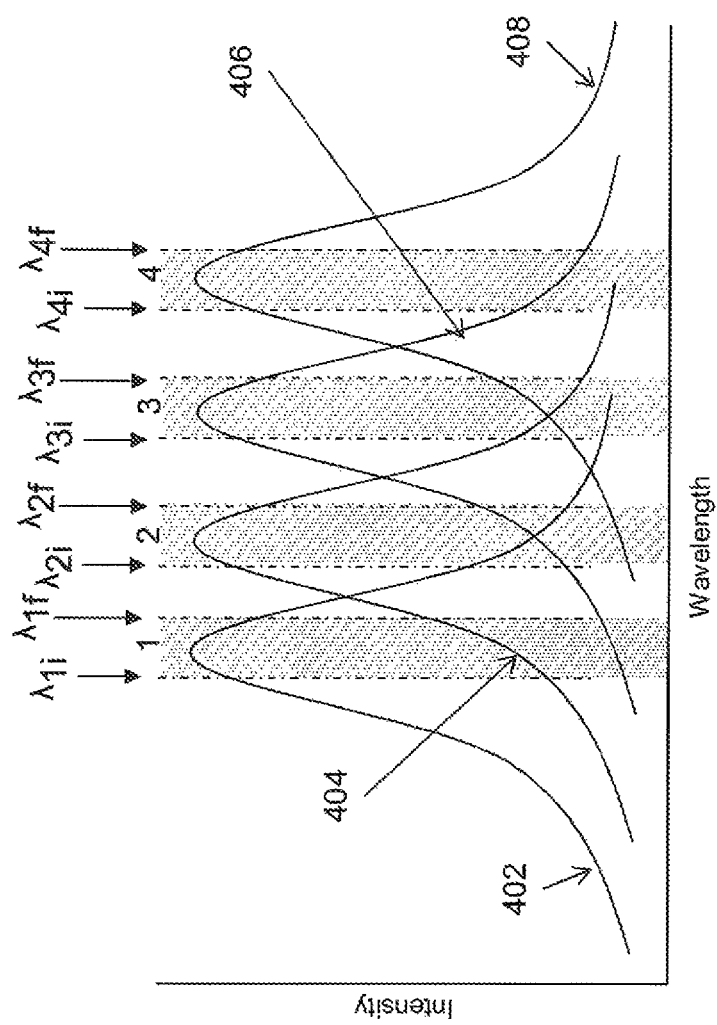
FIG. 4 schematically illustrates emission spectra of four distinct signal events, e.g., fluorescently labeled nucleotide analogs and illustrates the positions four blocking bands of the invention.

FIG. 4 illustrates an approach of the invention to blocking bands for four signals 402-408 where each of the signals has a maximum. In accordance with the invention as describe herein, it can be desirable to have a detection system for monitoring four spectrally distinct signals from a reaction region, by utilizing four blocking bands, each blocking band covering a wavelength region. Beginning from low wavelength to high wavelength, blocking band 1 blocks wavelengths from initial wavelength $\lambda 1i$ to final wavelength $\lambda 1f$; blocking band 2 blocks wavelengths from initial wavelength $\lambda 2i$ to final wavelength $\lambda 2f$; blocking band 3 blocks wavelengths from initial wavelength $\lambda 3i$ to final wavelength $\lambda 3f$; and blocking band 4 blocks wavelengths from initial wavelength $\lambda 4i$ to final wavelength $\lambda 4f$. In some cases, each of the blocking bands includes the wavelength corresponding to the position of maximum emission for each of the four signals in the reaction mixture. The position of the blocking bands and the spectral width of the blocking bands can be chosen to optimize performance.

In some cases the blocking bands do not overlap spectrally. In some cases, it is desirable to have the blocking bands wide enough to overlap spectrally. In some cases the bands will be adjacent to one another, e.g. where $\lambda 2f$ is substantially the same wavelength as $\lambda 3i$. It will be understood by those of skill in the art that widening the blocking band can provide for more effective blocking of the signal that the band corresponds to and therefore can help to discriminate one signal from another, and that narrowing of the band results in the collection of more photons which makes it more likely that a base that is in the detection volume will be seen as being present. These factors can be modified in order to obtain the best quality sequence data depending on the properties of the sequencing system.

In describing the blocking bands of the invention herein, the blocking bands have been described as having a distinct wavelength cutoff. It is understood that filters comprising blocking bands will have various levels of sharpness at the initial and at the final cutoff wavelength. For filters used in the invention, the wavelength cutoff can be set by a percentage of light transmitted at that wavelength. For example, the edge of a wavelength cutoff can be set by specifying a percentage of light that is transmitted at that wavelength. For example, where the edge of a wavelength filter drops to allowing only 1% of the light, this can be used as a measure of a wavelength cutoff for the purposes of the invention.

A system of the invention will typically have four sets of pixels, each of the four sets of pixels being blocked by a different color filter. Each of the filters will have at least one of the blocking bands. In the simplest case, filter 1 will have blocking band 1 from initial wavelength $\lambda 1i$ to final wavelength $\lambda 1f$, filter 2 will have blocking band 2 from initial wavelength $\lambda 2i$ to final wavelength $\lambda 2f$, filter 3 will have blocking band 3 from initial wavelength $\lambda 3i$ to final wavelength $\lambda 3f$, and filter 4 will have blocking band 4 from initial wavelength $\lambda 4i$ to final wavelength $\lambda 4f$.

In another approach of the invention, each of the filters has two blocking bands, and each filter has a different pair of blocking bands. For example, Filter 1 has blocking bands 1 and 2; filter 2 has blocking bands 2 and 3, filter 3 has blocking bands 3 and 4, and filter 4 has blocking bands 4 and 1. Any suitable combination of pairs of bands can be used. In some cases, some of the filters will have one blocking band and other filters will have two blocking bands.

In some aspect, the invention comprises a system for detecting a plurality of different optical signals from a reaction of interest, for example observing a nucleic acid sequencing reaction in real time. The system has an array of reaction regions each comprising a reaction mixture that produces 4 distinct optical signals, each of the 4 optical signals corresponding to one of 4 different reactive species, wherein an optical signal from one of the reactive species indicates a reaction event occurring with that reactive species. For example, each of the four optical signals can correspond to the presence of a single labeled nucleotide analog within a reaction region such as a zero mode waveguide. In order to monitor the reaction, one or more detectors is positioned in optical communication with the array of reaction regions comprising pixel subsets 1, 2, 3, and 4; wherein pixel subset 1 comprises filter 1 having wavelength blocking band 1 that blocks light from $\lambda 1i$ to $\lambda 1f$, pixel subset 2 comprises filter 2 that has wavelength blocking band 2 that blocks light from $\lambda 2i$ to $\lambda 2f$, pixel subset 3 comprises filter 3 that has wavelength blocking band 3 that blocks light from $\lambda 3i$ to $\lambda 3f$, pixel subset 4 comprises filter 4 that has wavelength blocking band 4 that blocks light from $\lambda 4i$ to $\lambda 4f$, wherein $\lambda 1i > \lambda 1f$, $\lambda 2i > \lambda 2f$, $\lambda 3i > \lambda 3f$, and $\lambda 4i > \lambda 4f$.

In some cases, there is one detector that has four sets of pixels, each set of pixels having above it a different filter such that emitted light from a reaction region passes through the filter to the detector below. It is generally desired that each of the wavelength blocking bands blocks 80% or greater of the light between wavelengths $\lambda i$ and $\lambda f$ for that band, and that each of the filters transmits 50%, 60%, 70%, 80% or greater of the light between $\lambda 1i$ and $\lambda 4f$ outside of its blocking band.

In some aspects the invention comprises a system for detecting a plurality of different optical signals from a reaction of interest such as a single molecule real time sequencing reaction where each of four filters has a different pair of blocking bands. The system has an array of reaction regions each comprising a reaction mixture that produces 4 distinct optical signals (402, 404, 406, 408), each of the 4 optical signals corresponding to one of 4 different reactive species, wherein an optical signal from one of the reactive species indicates a reaction event occurring with that reactive species. The four distinct optical signals can be provided, for example, but differentially labeled nucleotide analogs. In some cases, the range of wavelengths produced includes wavelengths between $\lambda 1i$ and $\lambda 4f$.

The system has one or more detectors positioned in optical communication with the array of reaction regions comprising pixel subsets 1, 2, 3, and 4; wherein pixel subset 1 comprises filter 1, pixel subset 2 comprises filter 2, pixel subset 3 comprises filter 3, pixel subset 4 comprises filter 4, wherein each of filters 1, 2, 3, and 4 comprises a pair of different wavelength blocking bands 1, 2, 3, or 4 wherein wavelength blocking band 1 blocks light from $\lambda 1i$ to $\lambda 1f$, wavelength blocking band 2 blocks light from $\lambda 2i$ to $\lambda 2f$, wavelength blocking band 3 blocks light from $\lambda 3i$ to $\lambda 3f$, wavelength blocking band 4 blocks light from $\lambda 4i$ to $\lambda 4f$, wherein $\lambda 1i > \lambda 1f \geq \lambda 2i > \lambda 2f \geq \lambda 3i > \lambda 3f \geq \lambda 4i > \lambda 4f$. Typically, each of the wavelength blocking bands blocks 80% or greater of the light between wavelengths $\lambda i$ and $\lambda f$ for that band, and each of the filter layers transmits 50%, 60%, 70%, 80% or greater of the light between $\lambda 1i$ and $\lambda 4f$ outside of the wavelength blocking bands for that filter, and the pair of wavelength blocking bands in each of the four filters is different from the pair of wavelength blocking bands in each of the filters.

The systems of the invention can be for example integrated devices in which the reaction region having a fluidic region in contact with them, illumination waveguides, and detectors are combined in a single inseparable unit. For example, each reaction region can emit light down to a portion of a detector below it, that portion of the detector having four distinct pixel subsets, each having a filter associated with it such that the emitted light from the reaction region passes through the filter to the detector.

Thus, the analytical devices of the invention provide for allowing more light per filter than conventional approaches. In one aspect, the invention provides an analytical device for detecting a plurality of different optical signals from reactions of interest where each reaction of interest has a number of reaction events occurring over a time. Such reaction events can be binding events in binding assays, or the incorporation of labeled nucleotide analogs. The integrated device has a substrate with an array of reaction regions. Each reaction region on the device has a reaction mixture that produces N distinct optical signals. N is typically 3 or greater. Each of the N optical signals corresponding to one of N different reactive species in the reaction mixture. As reactions occur within the reaction regions, an optical signal from one of the N reactive species indicates a reaction event occurring with that particular reactive species. The optical signals emitted by the N reactive species is detected by one or more detectors positioned in optical communication with the array of reaction regions for receiving the N distinct optical signals from each reaction region. The detector or detector region corresponding to a given reaction region has N different pixel subsets for each reaction region, where each of the N pixel subsets has a different filter that permits a fraction of greater than 1/N of light from the optical signals impinging upon the filter to pass through to the pixel subset.

Where there are four pixel subsets, for example, each of the N pixel subsets permits greater that 25% of the light impinging on the filter to pass through to the pixel subset. In some cases, more than 40% of the light impinging on each of the filters passes through to the pixel subset, and in some cases, more than 60% of the light impinging on each of the filters passes through to the pixel subset.

Nucleic Acid Sequencing

In a number of different nucleic acid sequencing analyses, fluorescently labeled nucleotides are used to monitor the polymerase-mediated, template-dependent incorporation of nucleotides in a primer extension reaction. In particular, a labeled nucleotide is introduced to a primer template polymerase complex, and incorporation of the labeled nucleotide is detected. If a particular type of nucleotide is incorporated at a given position, it is indicative of the underlying and complementary nucleotide in the sequence of the template molecule. In traditional Sanger sequencing processes, the detection of incorporation of labeled nucleotides utilizes a termination reaction where the labeled nucleotides carry a terminating group that blocks further extension of the primer. By mixing the labeled terminated nucleotides with unlabeled native nucleotides, one generates nested sets of fragments that terminate at different nucleotides. These fragments are then separated by capillary electrophoresis, to separate those fragments that differ by a single nucleotide, and the labels for the fragments are read in order of increasing fragment size to provide the sequence (as provided by the last added, labeled terminated nucleotide). By providing a different fluorescent label on each of the types of nucleotides that are added, one can readily differentiate the different nucleotides in the sequence (e.g., U.S. Pat. No. 5,821,058, incorporated herein for all purposes by this reference).

In newer generation sequencing technologies, arrays of primer-template complexes are immobilized on surfaces of substrates such that individual molecules or individual and homogeneous groups of molecules are spatially discrete from other individual molecules or groups of molecules, respectively. Labeled nucleotides are added in a manner that results in a single nucleotide being added to each individual molecule or group of molecules. Following the addition of the nucleotide, the labeled addition is detected and identified.

In some cases, the processes utilize the addition of a single type of nucleotide at a time, followed by a washing step. The labeled nucleotides that are added are then detected, their labels removed, and the process repeated with a different nucleotide type. Sequences of individual template sequences are determined by the order of appearance of the labels at given locations on the substrate.

In other similar cases, the immobilized complexes are contacted with all four types of labeled nucleotides where each type bears a distinguishable fluorescent label and a terminator group that prevents the addition of more than one nucleotide in a given step. Following the single incorporation in each individual template sequence (or group of template sequences,) the unbound nucleotides are washed away, and the immobilized complexes are scanned to identify which nucleotide was added at each location. Repeating the process yields sequence information of each of the template sequences. In other cases, more than four types of labeled nucleotides are utilized.

In particularly elegant approaches, labeled nucleotides are detected during the incorporation process, in real time, by individual molecular complexes. Such methods are described, for example, in U.S. Pat. No. 7,056,661, which is incorporated herein by reference in its entirety for all purposes. In these processes, nucleotides are labeled on a terminal phosphate group that is released during the incorporation process, so as to avoid accumulation of label on the extension product, and avoid any need for label removal processes that can be deleterious to the complexes. Primer/template polymerase complexes are observed during the polymerization process, and nucleotides being added are detected by virtue of their associated labels. In one particular aspect, they are observed using an optically confined structure, such as a zero mode waveguide (See, e.g., U.S. Pat. No. 6,917,726, which is incorporated herein by reference in its entirety for all purposes) that limits exposure of the excitation radiation to the volume immediately surrounding an individual complex. As a result, only labeled nucleotides that are retained by the polymerase during the process of being incorporated are exposed to excitation illumination for a time that is sufficient to identify the nucleotide. In another, approach, the label on the nucleotide is configured to interact with a complementary group on or near the complex, e.g., attached to the polymerase, where the interaction provides a unique signal. For example, a polymerase may be provided with a donor fluorophore that is excited at a first wavelength and emits at a second wavelength, while the nucleotide to be added is labeled with a fluorophore that is excited at the second wavelength, but emits at a third wavelength (See, e.g., U.S. Pat. No. 7,056,661, previously incorporated herein). As a result, when the nucleotide and polymerase are sufficiently proximal to each other to permit energy transfer from the donor fluorophore to the label on the nucleotide, a distinctive signal is produced. Again, in these cases, the various types of nucleotides are provided with distinctive fluorescent labels that permit their identification by the spectral or other fluorescent signature of their labels.

In the various exemplary processes described above, detection of a signal event from a reaction region is indicative that a reaction has occurred. Further, with respect to many of the above processes, identification of the nature of the reaction, e.g., which nucleotide was added in a primer extension reaction at a given time or that is complementary to a given position in a template molecule, is also achieved by distinguishing the spectral characteristics of the signal event.

The optical paths of the overall systems of the invention serve one or more roles of delivering excitation radiation to the reaction region, e.g., to excite fluorescent labeling molecules that then emit the relevant optical signal, conveying the optical signal emitted from the reaction region to the detector, and, for multispectral signals, i.e., multiple signals that may be distinguished by their emission spectrum, separating those signals so that they may be differentially detected, e.g., by directing different signals to different detectors, or different locations on the same detector array. The differentially detected signals are then correlated with both the occurrence of the reaction, e.g., a nucleotide was added at a given position, and the determination of the nature of the reaction, e.g., the added nucleotide is identified as a particular nucleotide type, such as adenosine.

In conventional analytical systems, the optical trains used to deliver excitation light to the reaction regions, and convey optical signals from the reaction regions to the detector(s) can impart size, complexity and cost aspects to the overall system that would preferably be reduced. For example, such optical trains may include collections of lenses, dispersion elements, beam splitters, beam expanders, collimators, spatial and spectral filters and dichroics, that are all assembled to deliver targeted and uniform illumination profiles to the different reactions regions. In large scale systems, these components must be fabricated, assembled, and adjusted to ensure proper alignment, focus, and isolation from other light and vibration sources to optimize the transmission of excitation light to the reaction regions. As the number of addressed reaction regions, or the sensitivity of the system to variations in excitation light intensity is increased, addressing these and other issues becomes more important, and again typically involves the inclusion of additional componentry to the optical train, e.g., alignment and focusing mechanisms, isolation structures, and the like.

With respect to the collection and detection of optical signals, conventional systems typically employ optical trains that gather emitted optical signals from the reaction region, e.g., through an objective lens system, transmit the various different signals through one or more filter levels, typically configured from one or more dichroic mirrors that differentially transmit and reflect light of different wavelengths, in order to direct spectrally different optical signals to different detectors or regions on a given detector. These separated optical signals are then detected and used to identify the nature of the reaction that gave rise to such signals. As will be appreciated, the use for such differential direction optics imparts substantial space, size and cost requirements on the overall system, in the form of multiple detectors, multiple lens and filter systems, and in many cases complex alignment and correlation issues. Many of these difficulties are further accentuated where the optical trains share one or more sub-paths with the excitation illumination, as signal processing will include the further requirement of separating out excitation illumination from each of the detected signals.

Again, as with the excitation optical train, above, as the sensitivity and multiplex of the system is increased, it increases the issues that must be addressed in these systems, adding to the complexity of already complex optical systems. Further, the greater the number of optical components in the optical train, the greater the risk of introducing unwanted perturbations into that train and the resulting ability to detect signal. For example, optical aberrations in optical elements yield additional difficulties in signal detection, as do optical elements that may inject some level of autofluorescence into the optical train, which then must be distinguished from the signaling events.

Integrated Devices

The present invention is directed, in part, to systems, devices and methods that utilize the filter architectures described herein within integrated detection and optical path components in small scale devices that optionally also include one or more of the reaction regions themselves, fluidic components for the reaction of interest, and excitation illumination paths and optionally excitation illumination sources. Integration of some or all of above described components into a single, miniaturized device addresses many of the problems facing larger, non-integrated analytical systems, such as size, cost, weight, inefficiencies associated with long path or free space optics, and the like.

Examples of such integrated systems are described, for example, in U.S. Published Patent Application Nos. 2012/0014837, 2012/0019828, and 2012/0021525, and Provisional Patent No. 61/738,637, filed Dec. 18, 2012, the entire contents of each of which are incorporated herein by reference in their entirety for all purposes. By integrating the detection elements with the reaction regions, either directly or as a coupled part, one can eliminate the need for many of the various components required for free space optics systems, such as much of the conveying optics, lenses, mirrors, etc., as well as, among other things, various alignment functionalities, as alignment is achieved through integration. The present invention seeks to further improve the benefits afforded by such devices by simplifying, to a greater extent, the optical components of the analytical devices, further reducing the cost and complexity of such devices and improving available signal in the process.

The analytical system in accordance with the present invention employs one or more analytical devices. In an exemplary embodiment, the system includes an array of analytical devices formed as a single integrated device. The exemplary array is configured for single use as a consumable. In various embodiments, the integrated optical element includes other components including, but not limited to local fluidics, electrical connections, a power source, illumination elements, a detector, logic, and a processing circuit. Each analytical device or array is configured for performing an analytical operation as described above.

Figure 5:
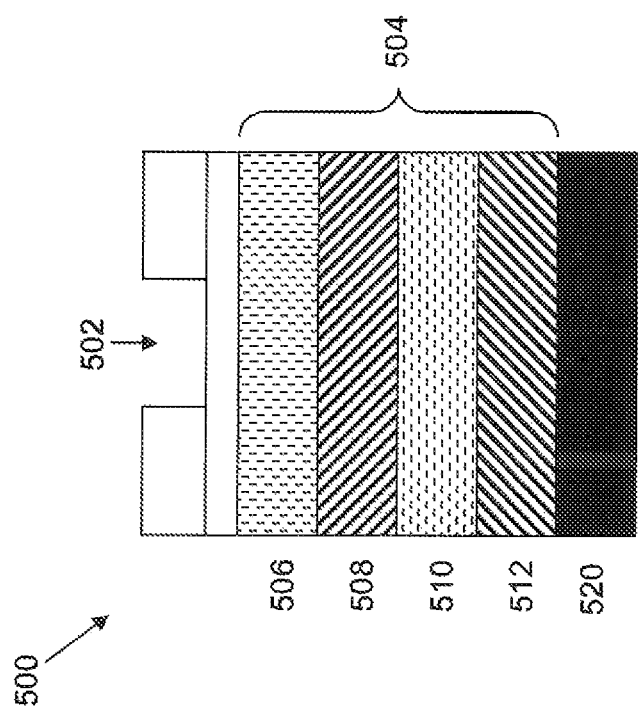
FIG. 5 provides a schematic block diagram of an integrated analytical device.

While the components of each device and the configuration of the devices in the system may vary, each analytical device can comprise, at least in part, the general structure shown as a block diagram in FIG. 5. As shown, an analytical device 500 typically includes a reaction cell 502, in which the reactants are disposed and from which the optical signals emanate. "Reaction cell" is to be understood as generally used in the analytical and chemical arts and refers to the location where the reaction of interest is occurring. Thus, "reaction cell" may include a fully self-contained reaction well, vessel, flow cell, chamber, or the like, e.g., enclosed by one or more structural barriers, walls, lids, etc., or it may comprise a particular region on a substrate and/or within a given reaction well, vessel, flow cell or the like, e.g., without structural confinement or containment between adjacent reaction cells. The reaction cell may include structural elements to enhance the reaction or its analysis, such as optical confinement structures, nanowells, posts, surface treatments, such as hydrophobic or hydrophilic regions, binding regions, or the like.

In various respects, "analytical device" refers to a reaction cell and associated components that are functionally connected. In various respects, "analytical system" refers to one or more associated analytical devices and associated components. In various respects, "analytical system" refers to the larger system including the analytical system and other instruments for performing an analysis operation. For example, in some cases, the analytical devices of the invention are part of an analytical instrument or analytical system. The analytical device can be removably coupled into the instrument. Reagents can be brought into contact with the analytical device before or after the analytical device is coupled with the system. The system can provide electrical signals and/or illumination light to the analytical device, and can receive electrical signals from the detectors in the analytical device. The instrument or system can have computers to manipulate, store, and analyze the data from the device. For example, the instrument can have the capability of identifying and sequences of added nucleotide analogs for performing nucleic acid sequencing. The identification can be carried out, for example, as described in U.S. Pat. No. 8,182,993, which is incorporated herein by reference for all purposes.

In some cases, one or more reactants for the reaction of interest may be immobilized, entrained or otherwise localized within a given reaction cell. A wide variety of techniques are available for localization and/or immobilization of reactants, including surface immobilization through covalent or non-covalent attachment, bead or particle based immobilization, followed by localization of the bead or particle, entrainment in a matrix at a given location, and the like. Reaction cells may include ensembles of molecules, such as solutions, or patches of molecules, or it may include individual molecular reaction complexes, e.g., one molecule of each molecule involved in the reaction of interest as a complex. Similarly, the overall devices and systems of the invention may include individual reaction cells or may comprise collections, arrays or other groupings of reaction cells in an integrated structure, e.g., a multiwall or multi-cell plate, chip, substrate or system. Some examples of such arrayed reaction cells include nucleic acid array chips, e.g., GeneChip® arrays (Affymetrix, Inc.), zero mode waveguide arrays (as described elsewhere herein), microwell and nanowell plates, multichannel microfluidic devices, e.g., LabChip® devices (Caliper Life Sciences, Inc.), and any of a variety of other reaction cells. In various respects, the "reaction cell", sequencing layer, and zero mode waveguides are similar to those described in U.S. Pat. No. 7,486,865 to Foquet et al., the entire contents of which are incorporated herein for all purposes by this reference. In some cases, these arrayed devices may share optical components within a single integrated overall device, e.g., a single waveguide layer to deliver excitation light to each reaction region. Approaches to illuminating analytical devices with waveguides are provided in U.S. Pat. Nos. 8,207,509, and 8,274,040 which are incorporated herein by reference for all purposes.

Although an analytical device may include an array of analytical devices having a single waveguide layer and reaction cell layer, one will appreciate that a wide variety of layer compositions may be employed in the waveguide array substrate and cladding/reaction cell layer and still achieve the goals of the invention (see, e.g., published U.S. Pat. No. 7,820,983, incorporated herein for all purposes by reference).

The analysis system typically includes one or more analytical devices 500 having a detector element 520, which is disposed in optical communication with the reaction cell 502. Optical communication between the reaction cell 502 and the detector element 520 may be provided by an optical train 504 comprised of one or more optical elements generally designated 506, 508, 510 and 512 for efficiently directing the signal from the reaction cell 502 to the detector 520. These optical elements may generally comprise any number of elements, such as lenses, filters, gratings, mirrors, prisms, refractive material, or the like, or various combinations of these, depending upon the specifics of the application. In addition to components for directing the optical signal from the reaction region to the detector, the chip can also have optical components for delivering illumination light to the reaction regions for performing fluorescent measurements.

In various embodiments, the reaction cell 502 and detector element 520 are provided along with one or more optical elements in an integrated device structure. By integrating these elements into a single device architecture, one improves the efficiency of the optical coupling between the reaction cell and the detector. As used herein, the term integrated, when referring to different components of an analytical device typically refers to two or more components that are coupled to each other so as to be immobile relative to each other. As such, integrated components may be irreversibly or permanently integrated, meaning that separation would damage or destroy one or both elements, or they may be removably integrated, where one component may be detached from the other component, provided that when they are integrated, they are maintained substantially immobile relative to one another. In some cases, the components are integrated together in one chip. In some cases, the detector portion is part of a separate instrument, and the reaction cell component is part of a chip. In the case where the reaction cell component is in a chip separate from the detector component, optical element components for directing the optical signal from the reaction cell to the detector can be in either the reaction cell component chip, in the detector component, or a combination in which some components are in the reaction cell component chip and others are in the detector.

For the devices, methods and systems of the invention, even where the detector is part of an instrument and separate from the reaction cell component chip, the chip will typically be placed directly onto the detector with a minimal open space between the reaction cell chip and the detector. In some cases, the space between the reaction cell chip and the detector will be less than 1 micron, less than 10 microns, less than 100 microns, or less than a millimeter.

The chip will typically have alignment structures to allow for the precise alignment of the reaction cells with the portions of the detector to which they correspond.

Where the reaction cell component, optical components, and detector are irreversibly or permanently integrated into a chip, such a chip can be produced by fabrication in a monolithic form, or two or more of the components can be manufactured separately and connected together to form the chip. The connection between the chip components can be accomplished by any suitable method including adhesion and wafer bonding.

The choice of whether to have all of the components integrated into a chip or to have the detector component separately associated with the instrument can be made depending on the application. A permanently integrated chip approach has the advantage that the detector can be manufactured in intimate contact with the reaction cell and other components under controlled conditions allowing for precise registration. The approach in which the detector is not integrated into the reaction cell chip, but is part of the instrument has the advantage that the detector can be used over and over again with different reaction cell chips.

In conventional optical analysis systems, discrete reaction vessels are typically placed into optical instruments that utilize free-space optics to convey the optical signals to and from the reaction vessel and to the detector. These free space optics tend to include higher mass and volume components, and have free space interfaces that contribute to a number of weaknesses for such systems. For example, such systems have a propensity for greater losses given the introduction of unwanted leakage paths from these higher mass components, and typically introduce higher levels of auto-fluorescence, all of which reduce the signal to noise ratio (SNR) of the system and reduce its overall sensitivity, which, in turn can impact the speed and throughput of the system. Additionally, in multiplexed applications, signals from multiple reaction regions (i.e., multiple reaction cells, or multiple reaction locations within individual cells), are typically passed through a common optical train, or common portions of an optical train, using the full volume of the optical elements in that train to be imaged onto the detector plane. As a result, the presence of optical aberrations in these optical components, such as diffraction, scattering, astigmatism, and coma, degrade the signal in both amplitude and across the field of view, resulting in greater noise contributions and cross talk among detected signals.

The analytical systems and devices in accordance with the present invention typically include a reaction region, vessel or zone that is either physically integrated with a detection component or sensor, or provided sufficiently proximal and in sensory communication with the detection component or sensor to improve performance.

Such devices have sought to take advantage of the proximity of the reaction region or vessel in which signal producing reactions are occurring, to the detector or detector element(s) that sense those signals, in order to take advantage of benefits presented by that proximity. As alluded to above, such benefits include the reduction of size, weight and complexity of the optical train, and as a result, increase the potential multiplex of a system, e.g., the number of different reaction regions that can be integrated and detected in a single device. Additionally, such proximity potentially provides benefits of reduced losses during signal transmission, reduced signal cross-talk from neighboring reaction regions, and reduced costs of overall systems that utilize such integrated devices, as compared to systems that utilize large free space optics and multiple cameras in signal collection and detection.

In the systems of the present invention, there are a number of design optimization criteria. For example, in the context of integrated detection systems, an over-arching goal is in the minimization of intervening optical elements that could interfere with the efficient conveyance of optical signals from the reaction region to the detector, as well as contribute to increased costs and space requirements for the system, by increasing the complexity of the optical elements between the reaction regions and the sensors.

Additionally, and with added importance for single molecule detection systems, it is also important to maximize the amount of optical signal that is detected for any given reaction event. In particular, in optical detection of individual molecular events, one is relying on a relatively small number of photons that correspond to the event of interest. While high quantum yield labeling groups, such as fluorescent dyes, can improve detectability, such systems still operate at the lower end of detectability of optical systems. Fluorescent dyes for analytical reactions are well known. Any suitable fluorescent dye can be used, for example, as described in 61/649,058 filed May 18, 2012—Heteroarylcyanine Dyes, US 20120058473—Molecular Adaptors for Dye Conjugates, US 20120077189—Scaffold-Based Polymerase Enzyme Substrates, US 20120052506—Cyanine Dyes, US 20120058469—Functionalized Cyanine Dyes (PEG), US 20120058482—Functionalized Cyanine Dyes ((Central Carbon), US 20100255488—Fret-Labeled Compounds and Uses Therefor, US 20090208957—Alternate Labelling Strategies for Single Molecule Sequencing In the context of the integrated devices and systems of the present invention, the size and complexity of the optical pathways poses a greater difficulty, as there is less available space in which to accomplish the goals of separation of excitation and signal, or separation of one signal from the next. Accordingly, the systems, devices and methods of the invention take advantage of simplified optical paths associated with the analyses being carried out, in order to optimize those analyses for the integrated nature of those devices and systems.

Figure 6:
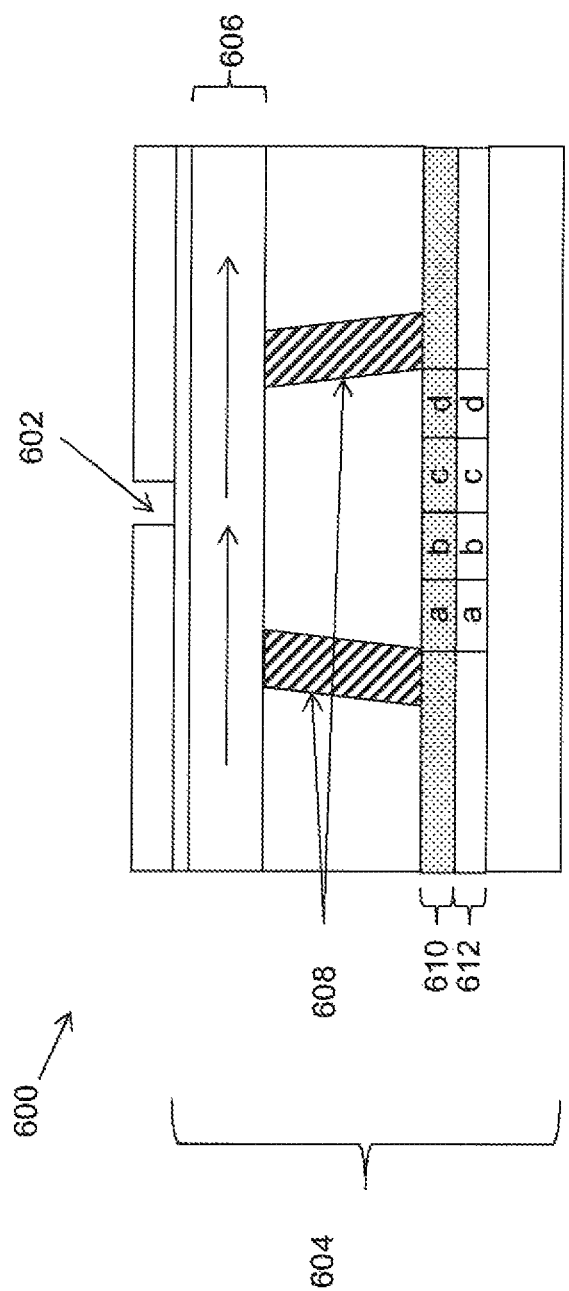
FIG. 6 schematically illustrates an integrated device for detecting signals.

FIG. 6 illustrates an example of a device architecture for performing optical analyses, e.g., nucleic acid sequencing processes or single molecule binding assay, that uses the filters of the present invention. As shown, an integrated device 600 includes a reaction region 602 that is defined upon a first substrate layer 604. As shown, the reaction region comprises a well 602 disposed in the substrate surface. Such wells may constitute depressions in a substrate surface or apertures disposed through additional substrate layers to an underlying transparent substrate, e.g., as used in zero mode waveguide arrays (See, e.g., U.S. Pat. Nos. 7,181,122 and 7,907,800). FIG. 6 illustrates a portion of a device having one reaction cell 602. Typically a device will have multiple reaction cells, for example thousands to millions or more reaction cells.

Excitation illumination is delivered to the reaction region from an excitation light source (not shown) that may be separate from or also integrated into the substrate. As shown, an optical waveguide (or waveguide layer) 606 is used to convey excitation light (shown by arrows) to the reaction region/well 602, where the evanescent field emanating from the waveguide 606 illuminates reactants within the reaction region 602. Use of optical waveguides to illuminate reaction regions is described in e.g., U.S. Pat. Nos. 7,820,983, 8,207,509, and 8,274,040, which is incorporated herein by reference for all purposes.

The integrated device 600 optionally includes light channeling components 608 to efficiently direct emitted light from the reaction regions to a detector layer 612 disposed beneath the reaction region. The detector layer will typically comprise multiple detector elements, for example the four detector elements 612a-d that are optically coupled to a given reaction region 602. For sequencing applications, often it is desirable to monitor four different signals in real time, each signal corresponding to one of the nucleobases. Although illustrated as a linear arrangement of pixels 612a-d, it will be appreciated that the detector elements may be arranged in a grid, n×n square, annular array, or any other convenient orientation. In some cases, each of the detector elements or channels will have a single pixel. In some cases, the detector elements will each comprise multiple pixels. The detector elements are connected electrically to conductors that extend out of the chip for providing electrical signals to the detector elements and for sending out signals from the detector elements.

Emitted signals from the reaction region 602 that impinge on these detector elements are then detected and recorded. As noted above, above each of the detector elements, each corresponding to a channel is disposed a color filter in filter layer 610. Here filter a corresponds to channel a, filter b corresponds to channel b, etc. As described in detail above, the set of filters is designed to allow for a high yield of captured photons, for example with each color filter having one or more blocking bands that block the signal from a portion of one or more of the spectrally distinct signals emitted from the reaction occurring in reaction region 602. As described herein, the filters are designed to allow a large percentage of the emitted photons while still discriminating between the four bases.

In some cases, optical elements are provided to selectively direct light from given sets of wavelengths to given detector elements. Typically, no specific light re-direction is used, such that the light reaching each of the filter layers the detector element is substantially the same.

The detector layer is then operably coupled to an appropriate circuitry, typically integrated into the substrate, for providing a signal response to a processor that is optionally included integrated within the same device structure or is separate from but electronically coupled to the detector layer and associated circuitry. Examples of types of circuitry are described in U.S. Published Patent Application No. 2012/0019828, previously incorporated herein.

Figure 7:
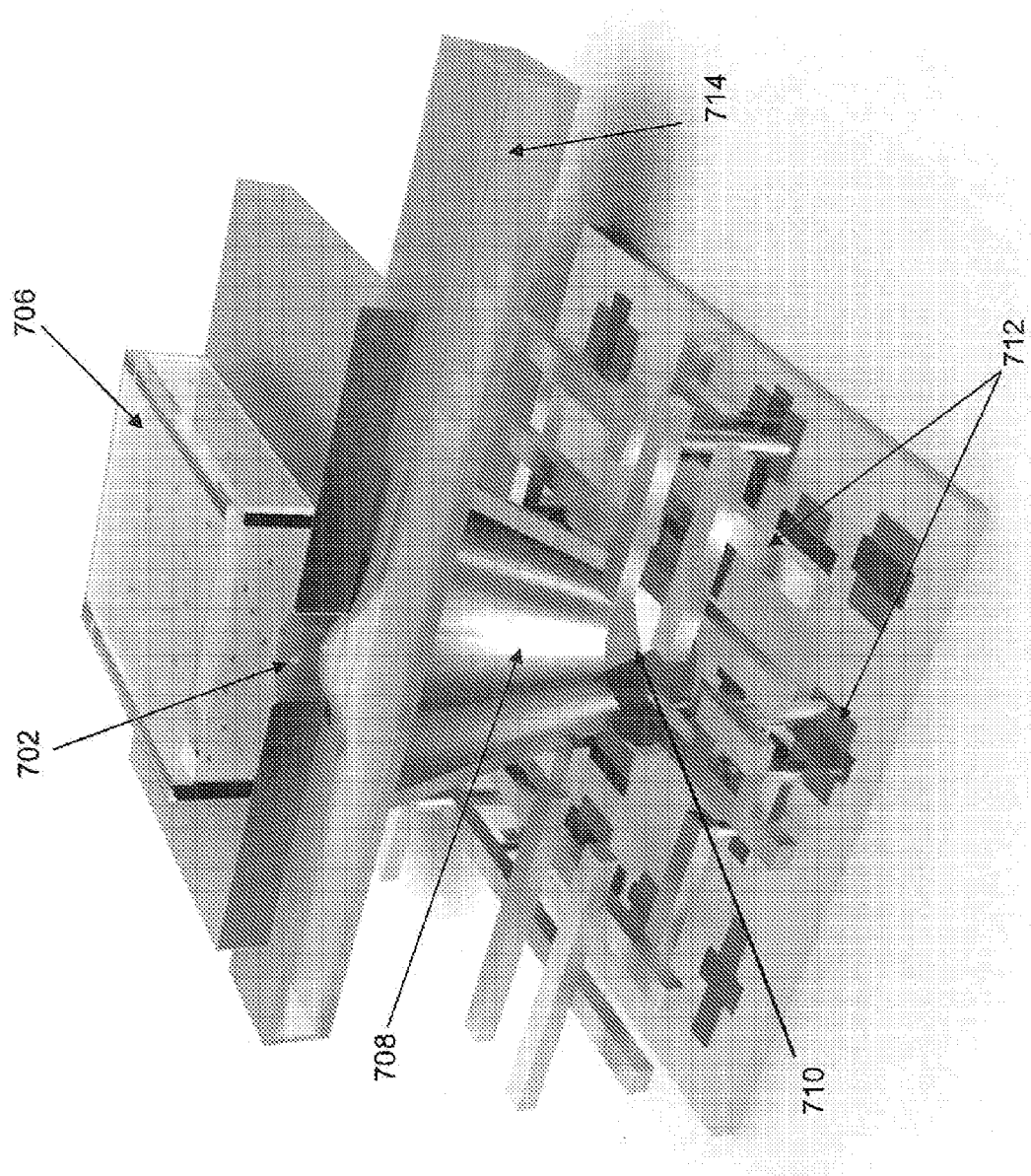
FIG. 7 schematically illustrates an exemplary structure for an integrated device.

With reference to an integrated device used for four color analyses, as alluded to above, an exemplary structure is shown in FIG. 7. As shown, the analytical device includes a reaction cell 702 that is coupled with a reagent reservoir or fluid conduit 706 which delivers reactants to the reaction cell 702. The reaction cell can be a nanoscale well or zero mode waveguide. In some cases, the reaction cell will have a biomolecule such as a polymerase enzyme immobilized within it. The fluidic conduit can provide reagents across a number of reaction cells. Below the reaction cell is a waveguide for providing excitation illumination to the reagents within the reaction cell. While a waveguide is shown here, other optical elements such as those provided elsewhere herein can be used to provide light from under the reaction cell. The illumination light can be used to excite fluorescent emission from reagents with the reactor cell. The light emitted from the reaction cell is directed downward through a transmission layer, which acts to transmit the light from the reaction cell to the detector. In some cases, the transmission layer will have optical components to enhance the efficiency of the light transfer or modulate the light. In the analytical device of FIG. 7, an optical tunnel or conduit 708 is disposed in optical communication with the reaction cell 702, which is in turn in optical communication with sensing elements 710 in the detector, where the light reaching each of the 4 sensing elements on the detector passes through a different filter. As shown, each reaction cell is optically coupled to a detector or detector element that includes 4 regions or pixel subsets, each region or pixel subset including a filter layer, and each filter layer including at least one blocking band as described herein. Each filter sends the appropriate set of wavelengths of light to the appropriate pixel subset shown as a discriminating region in FIG. 7. The pixel subsets or sensor elements are coupled to appropriate electronic components 712, such as busses and interconnects, that make up the overall sensor or camera. The electronic components can also include processing elements for processing the signal from the detectors.

Accordingly, in certain aspects, the present invention provides optical detection systems that reduce the attenuation of optical signals emanating from the reaction region and ultimately, that reach the detector. This permits detection and signal discrimination that is based upon a greater amount of emitted and detected signal.

Temporal Signal Distinction

In an alternative approach, the integrated systems of the invention simplify the optical path by relying on assay processes that utilize other than spectral separation of different signals to distinguish different signal events. Examples of such temporal signal distinction are described in U.S. Patent Application No. 2012/0019828, previously incorporated herein, and Published U.S. Patent Application No. 2009/0181396, incorporated herein by reference in its entirety for all purposes, and relies upon the use of different fluorescent labeling groups that possess distinct excitation spectra. By modulating the excitation light through each of the different excitation spectra, and correlating any resulting emitted fluorescence with the excitation spectrum at a given time, one can identify what excitation light caused a given emission, and consequently identify the fluorescent label and the reaction or reagent with which it is associated. As will be appreciated, this type of excitation and detection scheme requires no signal filtering optics, other than as necessary to screen out background or other incidental light, e.g., excitation illumination.

Again, as described above, in addition to benefits of increased signal at each detector, this aspect of the invention provides additional benefits in the context of integrated optical devices, e.g., devices in which at least the optical components, e.g., filters and the like, and detector elements are integrated into a single substrate. As will be noted, each of the above-described approaches provides an integrated device with a substantially simplified optical path, e.g., reduced filter sets and/or simplified excitation optics, over conventional multi-color signal discriminating optical systems. In particular, by providing a single filter type, rather than a filter stack between the assay location and a given detector, one can greatly simplify the overall architecture of the device. Further, because fewer layers are provided between the assay region and the detector, one can provide the assay location in closer proximity to the detector, reducing the potential for signal loss, cross-talk, and other signal transmission difficulties that may be inherent in more complex optical trains. In particular, where a more conventional four color system might require a four layer optical filter at each detector, and result in a substantially attenuated signal, the systems described herein would include a single filter layer at each detector, and result in the higher level signal profiles described above.

In the context of a number of aspects of the present invention, for systems that have greater than 2, greater than 3 or greater than 4 or more, spectrally distinct optical signals, the system will include a filter component that rejects or attenuates fewer than n−1 of those distinct optical signals, where n is the number of spectrally distinct signals, e.g., signals associated with different fluorescent label sets or different labeled reactants or reaction products. For example, with reference to the scheme described for FIGS. 6 and 7, above, a single signal attenuating filter, e.g., filter layer portion 710a in FIG. 7, may be used between the reaction region and a given detector, with a different single attenuating filter, e.g., filter layer portion 710b in FIG. 7, being provided over each of the four different detectors. Likewise, for a two color, two signal intensity signal profile for a given analysis, again a single signal attenuating filter element is provided over two of the detectors and a different single signal attenuating filter is provided over the other two detectors.

Analytical Instruments and Systems

Some aspects of the invention are analytical instruments for carrying out the methods and for use with the analytical devices described herein. For example, in some cases, the analytical devices of the invention are part of an analytical instrument or analytical system. The analytical device can be removably coupled into an instrument. Reagents are brought into contact with the analytical device before and/or after the analytical device is coupled with the instrument. The system or instrument can provide electrical signals and/or illumination light to the analytical device, and can receive electrical signals from the detectors in the analytical device. The instrument or system typically has computers to manipulate, store, and analyze the data from the device. For example, the instrument can have the capability of identifying and sequences of added nucleotide analogs for performing nucleic acid sequencing. The identification can be carried out, for example, as described in U.S. Pat. No. 8,182,993, and U.S. Published Patent Application Nos. 2010/0169026, and 2011/0183320 which are incorporated herein by references for all purposes.

For example, the invention includes analytical instruments comprising any suitable analytical device describe herein, an illumination source for providing illumination light to the one or more waveguides, an electronic system for providing voltage and current to the detector, and for receiving signals from the detector; and a computer system for analyzing the signals from the detector to monitor the analytical reaction, for example to obtain sequence information about a template nucleic acid.

Methods

The analytical devices of the invention described herein each provide methods for carrying out analytical reactions. Where combinations of filters are described herein, it would be understood by those of skill in the art that the invention comprises methods of carrying out analytical reactions using such devices.

For example the invention includes a method for detecting a plurality of different optical signals from reactions of interest each comprising a number of reaction events occurring over a time. The reaction events occur on a substrate with an array of reaction regions each having a reaction mixture that each produce N distinct optical signals wherein N is 3 or greater, each of the N optical signals corresponding to one of N different reactive species, where an optical signal from one of the N reactive species indicates a reaction event occurring with that reactive species. The N optical signals are detected at one or more detectors positioned in optical communication with the array of reaction regions for receiving the N distinct optical signals from each reaction region, the one or more detectors comprising N different pixel subsets for each reaction region. In this method, each of the N pixel subsets has a different filter that permits a fraction of greater than 1/N of light from the optical signals impinging upon the filter to pass through the pixel subset. Such methods are useful for following analytical reactions including single molecule binding reactions and sequencing.

In addition, the invention includes methods for monitoring analytical reactions that involve providing an analytical device having an array of reaction regions where each region has a reaction mixture characterized by the presence of N different labels. Each of the N different labels provides an emission spectrum having a maximum. The emitted signals are detected using one or more detectors. Each of the the one or more detectors has a plurality of pixels with N pixel subsets, wherein N is 3 or greater. Each pixel subset has a different filter with each filter having one or more blocking bands, each of which blocks a wavelength region including the emission maxima of from 1 to N−2 of the labels. Each filter blocks the emission maxima of a different label or of a different combination of labels than each other filter. The signals at each pixel subset are detected over time to monitor the analytical reaction.

The invention also includes methods of nucleic acid sequencing such as providing an analytical device having an array of reaction regions, each comprising a single immobilized polymerase enzyme complex comprising a polymerase enzyme and a primed template nucleic acid. Each reaction region has a reaction mixture characterized by the presence of 4 different fluorescent labels, where each label corresponds to one of four nucleotide analogs. Each of the labels provides an emission spectrum having a maximum. The array of reaction regions is illuminated using or more waveguides; and the emission spectra are detected with a detector comprising a plurality of pixels with 4 pixel subsets for each reaction region. Each of the 4 pixel subsets has a different filter with one or more blocking bands that each block a wavelength region including the emission maxima of one or two, but not three of the 4 labels, and each blocking filter blocks the emission maxima of a different label or of a different combination of labels. Typically, each of the filters permits greater than 25% of light from the optical signals impinging upon the filters to pass through. In some cases it is desirable for each of the filters to permit greater than 40% of light from the optical signals impinging upon the filters to pass through. In some cases each of the filters permits greater than 60% of light from the optical signals impinging upon the filters to pass through. The methods of the invention are particularly useful for integrated devices having components that are irreversibly integrated.

What is claimed is:

1. An analytical device, comprising:
    an array of reaction regions, each comprising a reaction mixture that produces 3 or more distinct optical signals based upon the occurrence of different reaction events, wherein the 3 or more optical signals correspond to different labels, each label providing a different emission spectrum, each emission spectrum having a maximum;
    one or more detectors in optical communication with the array of reaction regions, the one or more detectors comprising multiple pixel subsets, wherein the number of pixel subsets is the same as the number of different labels; and
    a different filter for each pixel subset, wherein each different filter has one or more blocking bands which:
        blocks a wavelength region including the emission maxima of at least one of the different labels, and
        allows through a wavelength region including the emission maxima of multiple of the different labels;
    wherein each different filter blocks the emission maxima of a different one of the different labels or of a different combination of the different labels than each of the other different filters, and wherein the one or more detectors are configured to detect the emission spectra for each of the array of reaction regions to obtain a signal profile of the multiple pixel subsets, wherein the signal profile uniquely identifies the label that produced the detected emission spectra, which correlates with the occurrence of one of the different reaction events.

2. The analytical device of claim 1 wherein each of the different filters blocks the emission maximum of a different one of the different labels.

3. The analytical device of claim 1 wherein the reaction mixture produces 4 distinct optical signals corresponding to 4 different labels.

4. The analytical device of claim 3 wherein each of the different filters blocks the emission maximum of a different combination of two of the different labels.

5. The analytical device of claim 3 for nucleic acid sequencing wherein the reaction regions each comprise a single polymerase enzyme complex comprising a polymerase enzyme and a template nucleic acid.

6. The analytical device of claim 5 wherein each different label corresponds to one of four nucleotide analogs.

7. The analytical device of claim 6 wherein the different labels are different fluorescent labels, the emission spectra comprises fluorescent signals, and the analytical device further comprises one or more waveguides for illumination of the array of reaction regions.

8. An analytical instrument comprising:
    the analytical device of claim 7;
    an illumination source for providing illumination light to the one or more waveguides;
    an electronic system for providing voltage and current to the detector, and for receiving signals from the detector; and
    a computer system for analyzing the signals from the detector to obtain sequence information about the template nucleic acid.

9. The analytical device of claim 1 having one detector.

10. The analytical device of claim 9 wherein the array of reaction regions is integrated with the detector.

11. The analytical device of claim 9 wherein the array of reaction regions is irreversibly integrated with the detector.

12. The analytical device of claim 1 wherein the emission spectra comprise fluorescent signals and the analytical device further comprises an integrated waveguide for illumination of the array of reaction regions.

13. A method for monitoring an analytical reaction for a reaction event, comprising:
    providing an analytical device having:
        an array of reaction regions, each comprising a reaction mixture that produces 3 or more distinct optical signals based upon the occurrence of different reaction events, wherein the 3 or more optical signals correspond to different labels, each label providing a different emission spectrum, each emission spectrum having a maximum;
        one or more detectors in optical communication with the array of reaction regions, the one or more detectors comprising multiple pixel subsets, wherein the number of pixel subsets is the same as the number of different labels; and
        a different filter for each pixel subset, wherein each different filter has one or more blocking bands which:
            blocks a wavelength region including the emission maxima of at least one of the different labels, and
            allows a wavelength region including the emission maxima of multiple of the different labels through;
        wherein each different filter blocks the emission maxima of a different one of the different labels or of a different combination of the different labels than each of the other different filters;
    detecting the emission spectra for each of the array of reaction regions with the one or more detectors to obtain a signal profile of the multiple pixel subsets;
    identifying the label that produced the detected emission spectra for each of the array of reaction regions based on the signal profile; and
    correlating the identified label with the occurrence of one of the different reaction events, thereby monitoring the analytical reaction for a reaction event.

14. The method of claim 13 wherein each of the different filters blocks the emission maximum of a different one of the different labels.

15. The method of claim 13 wherein the reaction mixture produces 4 distinct optical signals corresponding to 4 different labels.

16. The method of claim 15 wherein each of the different filters blocks the emission maximum of a different combination of two of the different labels.

17. The method of claim 15 wherein the method is a method for nucleic acid sequencing, wherein the reaction regions each comprise a single polymerase enzyme complex comprising a polymerase enzyme and a template nucleic acid.

18. The method of claim 17 wherein each different label corresponds to one of four nucleotide analogs.

19. The method of claim 18 wherein the different labels are different fluorescent labels, the emission spectra comprises fluorescent signals, and the analytical device further comprises one or more waveguides for illumination of the array of reaction regions.

20. The method of claim 13 wherein the analytical device has one detector.

21. The method of claim 20 wherein the array of reaction regions is integrated with the detector.

22. The method of claim 20 wherein the array of reaction regions is irreversibly integrated with the detector.

23. The method of claim 13 wherein the analytical device further comprises an integrated waveguide for illumination of the array of reaction regions, the method further comprising illuminating the array of reaction regions with one or more excitation wavelength of light via the integrated waveguide, wherein the emission spectra comprise fluorescent signals.

* * * * *